US006983034B2

(12) United States Patent
Wang et al.

(10) Patent No.: US 6,983,034 B2
(45) Date of Patent: Jan. 3, 2006

(54) METHODS AND DEVICES FOR CT RECONSTRUCTION USING A GRANGEAT APPROACH

(75) Inventors: Ge Wang, Iowa City, IA (US); Seung Wook Lee, Daejeon (KR)

(73) Assignee: University of Iowa Research Foundation, Iowa City, IA (US)

( * ) Notice: Subject to any disclaimer, the term of this patent is extended or adjusted under 35 U.S.C. 154(b) by 36 days.

(21) Appl. No.: 10/780,916

(22) Filed: Feb. 17, 2004

(65) Prior Publication Data

US 2004/0240604 A1 Dec. 2, 2004

Related U.S. Application Data

(60) Provisional application No. 60/447,580, filed on Feb. 14, 2003.

(51) Int. Cl.
*A61B 6/00* (2006.01)

(52) U.S. Cl. .............................. 378/4; 378/15; 378/901
(58) Field of Classification Search .................... 378/4, 378/15, 19, 901
See application file for complete search history.

(56) References Cited

U.S. PATENT DOCUMENTS

| 5,170,439 A | 12/1992 | Zeng et al. |
| 5,341,460 A | 8/1994 | Tam |
| 5,404,293 A | 4/1995 | Weng et al. |

(Continued)

FOREIGN PATENT DOCUMENTS

| EP | 0 492 895 A2 | 7/1992 |
| EP | 0 573 364 A1 | 12/1993 |
| EP | 0 592 093 A2 | 4/1994 |
| WO | WO 98/30980 | 1/1998 |
| WO | WO 99/01066 | 1/1999 |

OTHER PUBLICATIONS

"Guest Editorial Multirow Detector and Cone–Beam Spiral/Helical CT", Wang et al., *IEEE Transactions On Medical Imaging*, vol. 19, No. 9, Sep. 2000, pp 817–821.

"A Grangeat–type half–scan algorithm for cone–beam CT", Lee et al., *Med. Phys.*, vol. 30, No. 4, Apr. 2003, pp. 689–700.

"Grangeat–type helical half–scan computerized tomography algorithm for reconstruction of a short object", Lee et al., *Med. Phys.*, vol. 31, No. 1, Jan. 2004, pp 4–16.

(Continued)

*Primary Examiner*—Edward J. Glick
*Assistant Examiner*—Elizabeth Keaney
(74) *Attorney, Agent, or Firm*—Needle & Rosenberg, P.C.

(57) ABSTRACT

An image of an object is reconstructed in a three-dimensional coordinate system in an x-ray computed tomography system. A partial scan of the object is performed by rotating an x-ray beam having a cone beam geometry around a portion of the object or rotating the object in the cone-beam. The x-ray beam forms on a scanning trajectory through a plurality of projection lines from a plurality of successive focal point locations. The scanning trajectory may be substantially circular, helical, spiral, or spiral-like. The x-ray beam, attenuated by the object during the spiral scan, is detected to produce detector values. The detector values are integrated along straight lines on the detector plane to obtain intermediate data. Three-dimensional Radon values representing approximate plane integrals of the object are calculated from the intermediate data using a Grangeat relationship or a modified or extended version or the Grangeat relationship. The calculated and estimated Radon values are then reconstructed into an image volume according to the Radon inversion formula.

30 Claims, 25 Drawing Sheets

U.S. PATENT DOCUMENTS

| | | | |
|---|---|---|---|
| 5,408,511 | A | 4/1995 | Grangeat et al. |
| 5,446,776 | A | 8/1995 | Tam |
| 5,907,594 | A | 5/1999 | Lai |
| 5,909,476 | A | 6/1999 | Cheng et al. |
| 5,930,384 | A | 7/1999 | Guillemaud et al. |
| 5,960,056 | A | 9/1999 | Lai |
| 5,995,580 | A | 11/1999 | Schaller |
| 5,999,587 | A * | 12/1999 | Ning et al. ............. 378/4 |
| 6,075,836 | A | 6/2000 | Ning |
| 6,219,441 | B1 | 4/2001 | Hu |
| 6,298,110 | B1 * | 10/2001 | Ning ................... 378/4 |
| 6,301,325 | B1 | 10/2001 | Besson et al. |
| 6,332,035 | B1 | 12/2001 | Basu et al. |
| 2002/0118790 | A1 | 8/2002 | Pan et al. |

OTHER PUBLICATIONS

"Half–scan cone–beam CT fluoroscopy with multiple x–ray sources", Liu et al., *Med. Phys.*, vol. 28, No. 7, Jul. 2001, pp 1466–1471.

"Image reconstruction from fan–beam projections on less than a short scan", Noo et al., *Phys. Med. Biol.*, vol. 47, 2002, pp 2525–2546.

"A Cone–Beam Reconstruction Algorithm Using Shift–Variant Filtering and Cone–Beam Backprojection", Defrise et al., *IEEE Transactions On Medical Imaging*, vol. 13, No. 1, Mar. 1994, pp 186–195.

"A General Cone–Beam Reconstruction Algorithm", Wang et al., *IEEE Transactions On Medical Imaging*, vol. 12, No. 9, Sep. 1993, pp 486–496.

"Theoretically Exact Filtered Backprojection–Type Inversion Algorithm For Spiral CT", Alexander Katsevich, *SIAM J. Appl. Math*, vol. 62, No. 6, 2002, pp 2012–2026.

"Microlocal Analysis of an FBP Algorithm for Truncated Spiral Cone Beam Data", Alexander Katsevich, *The Journal of Fourier Analysis and Applications*, vol. 8, Issue 5, 2002 pp 407–425.

"Mathematical Framework Of Cone Beam 3D Reconstruction Via The First Derivative Of The Radon Transform", Pierre Grangeat, *Leti/Dsys/Setia/100392/C433–1*, Mar. 10, 1992, pp 1–32.

"Artifacts associated with implementation of the Grangeat formula", Lee et al., *Med. Phys.*, vol. 29, No. 12, Dec. 2002, pp 2871–2880.

\* cited by examiner

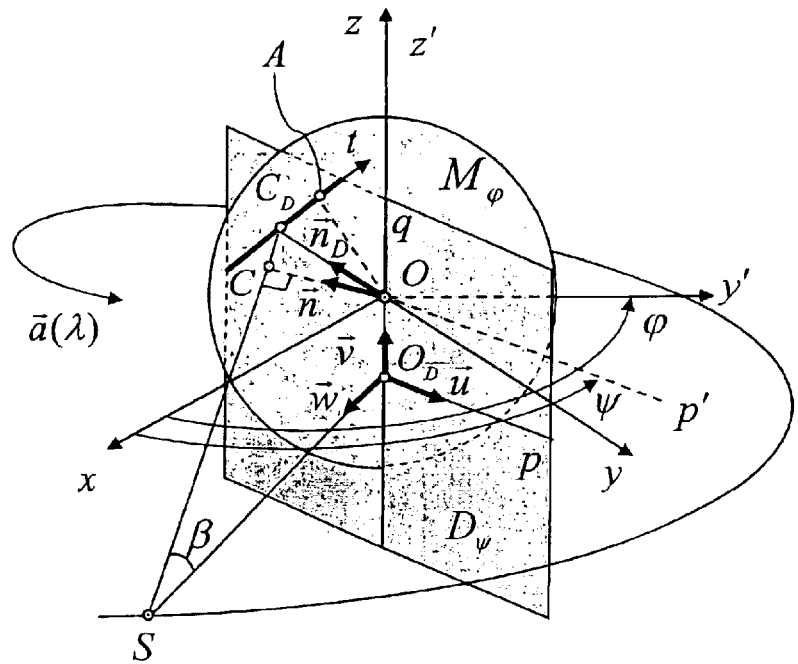
FIG. 16(a)
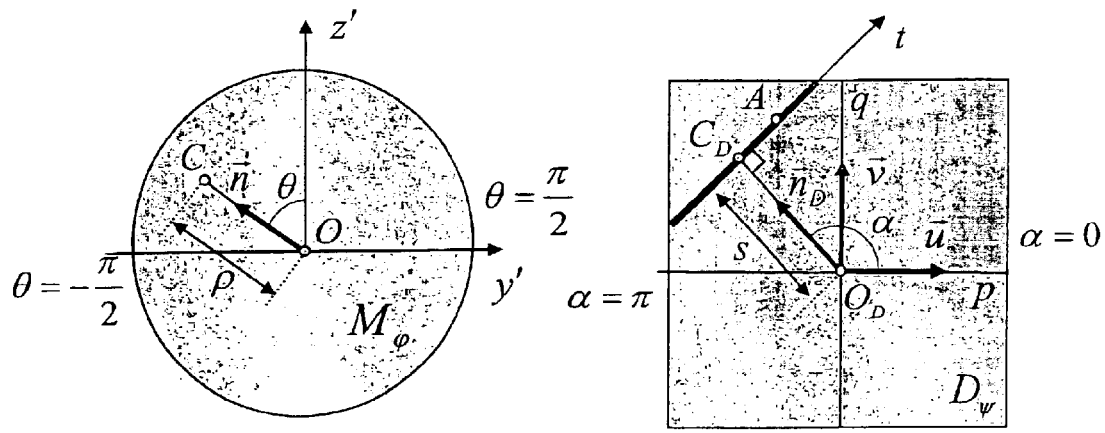
FIG. 16(b)
FIG. 16(c)

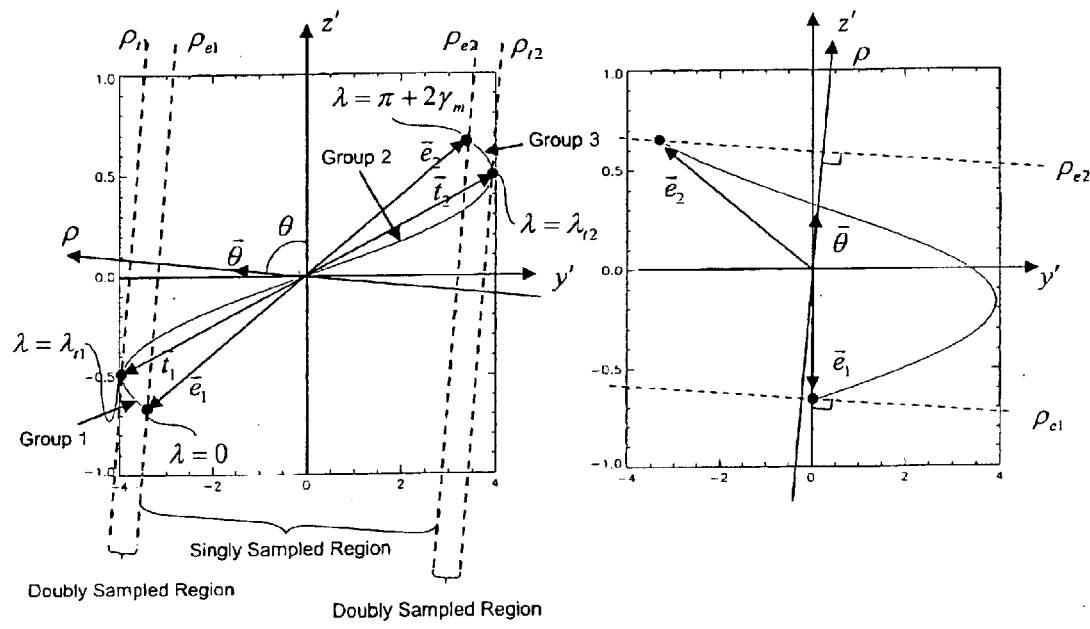
FIG. 20(a)        FIG. 20(b)
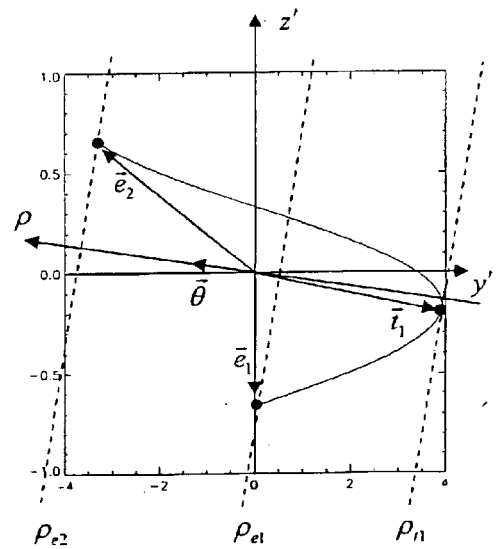 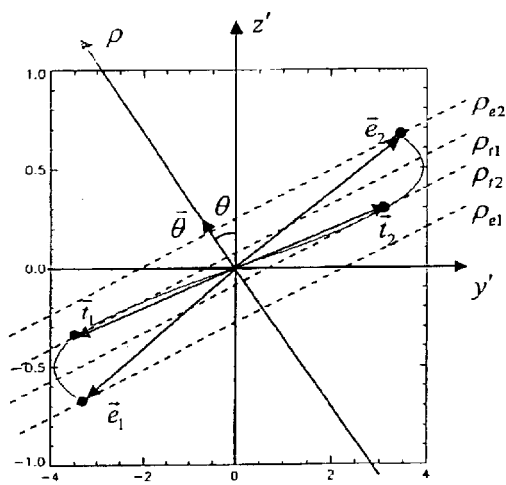
FIG. 20(c)        FIG. 20(d)

METHODS AND DEVICES FOR CT RECONSTRUCTION USING A GRANGEAT APPROACH

CROSS REFERENCE TO RELATED APPLICATION

This application claims priority to U.S. Provisional Application No. 60/447,580 filed Feb. 14, 2003, and hereby incorporated by reference.

STATEMENT REGARDING FEDERALLY SPONSORED RESEARCH OR DEVELOPMENT

This invention was made with government support under NIH Grants R01 DC03590 and EB001685. The government may have certain rights in the invention.

BACKGROUND

This invention relates to methods and devices for volumetric computed tomograph (CT) reconstruction and more specifically to methods and devices for Grangeat-type half-scan cone beam volumetric CT reconstruction for short and long objects in the helical and circular scanning cases.

In at least one known CT imaging system configuration, an x-ray source projects a fan-shaped beam which is collimated to lie within an X-Y plane of a Cartesian coordinate system, generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In other known CT systems, the x-ray source and the detector array are rotated with a gantry within the imaging plane and around the object to be imaged so that the angle at which the x-ray beam intersects the object constantly changes. A group of x ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object.

One method for reconstructing an image from a set of projection data is referred to in the art as the filtered back-projection technique. This process converts the attenuation measurements from a scan into integers called "CT numbers" or "Hounsfield units", which can be used to control the brightness of a corresponding pixel on a cathode ray tube display.

The two-dimensional methods discussed above can reconstruct a slice of the measured object. If a volume segment needs to be reconstructed, the complete procedure can be performed slice-by-slice with a small movement of the object or of the source-detector system between each slice.

A more efficient acquisition setup for volumetric CT uses a two-dimensional detector. The rays then form a cone with its base on the detector and its apex on the source. An x-ray source naturally produces a cone of rays, so cone-beam acquisition not only increases the scanning speed, but also makes better use of the emitted rays otherwise wasted by collimation.

Modern CT scanners are rapidly moving from fan-beam towards cone-beam geometry. Current micro-CT scanners are already in cone-beam geometry. Half-scan CT algorithms are advantageous in terms of temporal resolution and are widely used in fan-beam and cone-beam geometry.

A helical source trajectory is natural for volume scanning of long objects. A continuously translated object and a rotating source-detector system yield a helical source trajectory around the object. Helical scanning has been used for many years with one-dimensional detectors and has now been extended for use with multi-row detectors with potential applications for two-dimensional detectors in the medical imaging field.

Sixteen-slice helical computerized tomography scanners are commercially available. An efficient way to acquire volumetric patient data is to use a helical source trajectory together with a multi-row detector.

With the increasing number of detector rows, the cone-beam CT systems are expected to be available in the near future. New applications made possible by these new fast volumetric imaging technologies include, but are not limited to, cardiac and lung examinations, CT angiography, and interventional procedures. In those applications, high temporal resolution is one of the most important requirements.

Half-scan techniques have been developed to improve the temporal resolution for axial and spiral CT images. Various half-scan cone-beam reconstruction methods are known in the art.

The first practical algorithm for three-dimensional reconstruction from cone beam projections acquired from a circular source trajectory was the Feldkamp method. Various Feldkamp-type algorithms were developed for half-scan cone-beam reconstructions from half-scan data collected from circular and helical loci. This method has certain limitations, most notably off-mid-plane artifacts that occur because the approximation error becomes larger as it goes away from the mid-plane.

It is therefore desirable to provide a method and apparatus for a half-scan cone-beam, three dimensional reconstruction of computed tomographic images that performs appropriate data filling using the Grangeat approach and suppresses the off-mid-plane artifacts associated with the Feldkamp-type algorithms.

SUMMARY

The present invention is directed to methods and devices for volumetric CT reconstruction. According to an exemplary embodiment, the device may include a system processor that supports the desired functionality as described in detail below and a system data store (SDS) that stores data associated with this functionality, such as Grangeat-type half-scan cone beam volumetric CT reconstruction data.

The system processor is in communication with the SDS. The SDS may include multiple physical and/or logical data stores for storing the various types of information used. Data storage and retrieval functionality can be provided by either the system processor or one or more data storage processors associated with the SDS. The system processor may communicate with the SDS via any suitable communication channel(s). The system processor may include one or more processing elements that are adapted or programmed to support the desired image reconstruction and/or other functionality.

Currently, cone-beam CT and Micro-CT scanners are under rapid development for major biomedical applications. Half-scan cone-beam image reconstruction algorithms assume only part of a scanning turn, and are advantageous in terms of temporal resolution and image artifacts. While half-scan cone-beam algorithms known in the art are in the Feldkamp framework, according to exemplary embodiments a half-scan algorithm in the Grangeat framework is used for circular and helical trajectories.

According to exemplary embodiments, a method of image reconstruction includes a variety of steps that may, in certain embodiments, be executed by the environment summarized above and more fully described below or be stored as computer executable instructions in and/or on any suitable combination of computer-readable media.

According to one embodiment, a half-scan algorithm is used for image reconstruction for a circular scanning case. The half-scan spans 180 degrees plus two cone angles that provide sufficient data for reconstruction of the mid-plane defined by the source trajectory. A generalized half-scan, such as a so-called extended half scan, is also possible. Smooth half-scan weighting functions are used for suppression of data inconsistencies in some embodiments. Numerical simulation results are reported for verification of formulas and programs of the present invention. This Grangeat-type half-scan algorithm produces excellent image quality, without off-mid-plane artifacts associated with Feldkamp-type half-scan algorithms. The Grangeat-type half-scan algorithm can be used for quantitative and dynamic biomedical CT and micro-CT applications.

In another embodiment, image reconstruction may be implemented in a helical case without data truncation. According to this embodiment, Grangeat's formula is modified for utilization and estimation of Radon data. Specifically, each characteristic point in the Radon space can be categorized into singly, doubly, triply sampled, and shadow regions. A smooth weighting strategy can be used to compensate for data redundancy and inconsistency in some embodiments.

In the helical half-scan case, the projected trajectories and transition points on meridian planes are introduced to guide the design of weighting functions. Then, the shadow region is recovered via linear interpolation after smooth weighting. The Shepp-Logan phantom and other phantoms can be used to verify the correctness of the formulation. The Grangeat-type helical half-scan algorithm of the present invention is not only valuable for quantitative and/or dynamic biomedical applications of CT and micro-CT, but it can also serve as a basis for solving the long object problem in the Grangeat framework.

Additional advantages of the invention will be set forth in part in the description which follows, and in part will be obvious from the description, or may be learned by practice of the invention. It is to be understood that both the foregoing general description and the following detailed description and the description in the attachments hereto are exemplary and explanatory only and are not restrictive of the invention.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 3($a$) shows a relationship between meridian and detector planes, FIG. 3($b$) illustrates a meridian plane, and FIG. 3($c$) illustrates a detector plane;

FIG. 11($c$) illustrates exemplary comparative profiles from the identical positions marked by the dashed line in 11($a$);

FIG. 13($c$) illustrates exemplary comparative profiles from the identical positions marked by the dashed line in FIG. 13($a$);

FIG. 14($d$) illustrates exemplary comparative profiles from the identical positions marked by the dashed line in FIG. 14($a$);

FIGS. 16($a$)–($c$) depict another illustration of exemplary meridian and detector planes with a helical scanning locus explicitly drawn. FIG. 16($a$) shows a relationship between meridian and detector planes, FIG. 16($b$) illustrates a meridian plane, and FIG. 16($c$) illustrates a detector plane, all of which are in the context of a helical scanning locus;

FIGS. 20(a)–(d) illustrate exemplary transition points for design of the weighting functions on meridian planes are shown, and in FIGS. 20(b)–(d), case i, case ii, and case viii are shown, respectively;

In FIGS. 21(a), (e), (i), the region map is the brightest for triply sampled zones and the darkest shadow zone. In FIGS. 21(b), (f), (j), the region map is the brightest for the first weighting distribution. In FIGS. 21(c), (g), (k), the region map is the brightest for the second weighting distribution, and in FIGS. 21(d), (h), (l), the region map is the brightest for the third weighting distribution;

DETAILED DESCRIPTION

Figure 1:
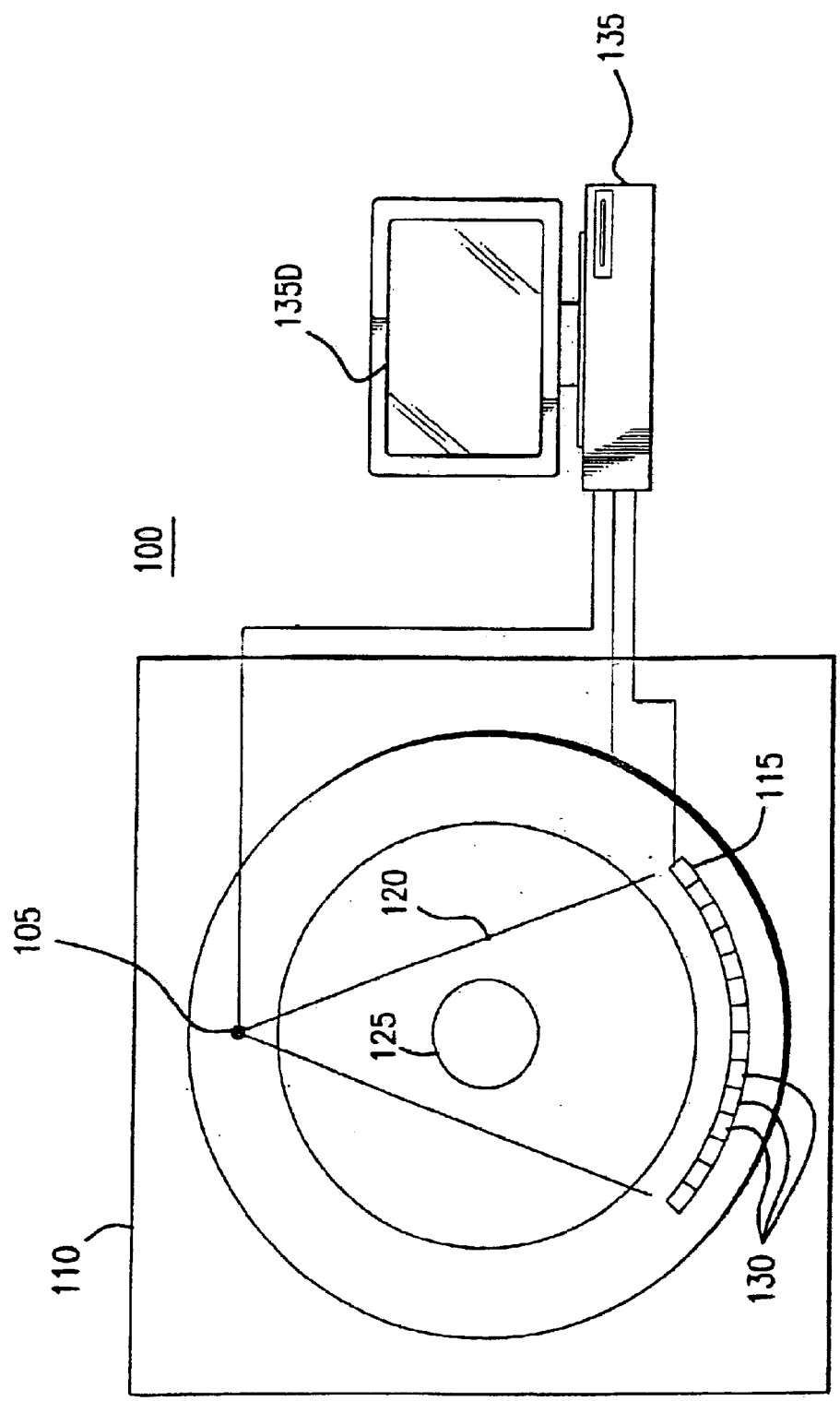
FIG. 1 illustrates an exemplary device and system for image reconstruction of an object.

One or more exemplary embodiments are now described in detail hereinbelow and illustrated in the attached drawings. Referring to the drawings, like numbers indicate like parts throughout the views. As used in the description herein, the meaning of "a," "an," and "the" includes plural reference unless the context clearly dictates otherwise. Also, as used in the description herein, the meaning of "in" includes "in" and "on" unless the context clearly dictates otherwise. Finally, as used in the description herein, the meanings of "and" and "or" include both the conjunctive and disjunctive and may be used interchangeably unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

According to an exemplary embodiment, the invention can be implemented in conjunction with an x-ray tomographic system, such as that depicted schematically in FIG. 1. While an exemplary system using x-rays is described below, one skilled in the art will appreciate that the cone-beam algorithms could be used, with or without modification as necessary, in conjunction with other imaging modalities that involve cone-beam geometry, including but not limited to PET and SPECT scanners.

As shown in FIG. 1, the x-ray tomographic system 100 that can be used in the present invention uses a gantry 110. The gantry 110 contains an x-ray point source 105 that projects a beam 120 at a detector array 115 on the opposite side of the gantry 110. The beam 120 passes through the subject 125, and the individual detectors 130 within the detector array 115 sense the attenuation of the beam 120 passing through the subject 125. The detectors 130 generate electrical signals corresponding to the attenuation, and the x-ray source and detector assembly rotates about the subject 120 to generate projection data.

Detector array 115 is formed by detector elements or cells 130 which together sense the projected x-rays that pass through an object 125, for example a patient. Detector array 115 may be fabricated in a single slice or multi-slice configuration, and also, in various shapes, such as an arc of a circle, an arc of a cylinder, or flat panels. The detectors 130 can transmit the projection data to the computer system 135 or other system processor or processors, which can reconstruct an image from the projection data. The computer 135 can, in some embodiments, transmit this image to a subsystem for display, and possible archiving, which in one embodiment can be the computer's display 135D. In one embodiment, the computer 135 can be a Silicon Graphics O2 computing platform (Silicon Graphics, Inc.; Mountain View, Calif., USA), or any other suitable single or multiprocessor computing system such as those further described herein below.

The image reconstruction systems and methods can be executed on one or more system processors. Additionally, the systems and methods can be programmed in any programming language that one skilled in the art would find appropriate. In one embodiment, the system can be programmed in IDL (Interactive Data Language from Research Systems, Boulder, Colo., USA).

Rotation of gantry 110 and the operation of x-ray source 105 are governed by a control mechanism of CT system 100. The control mechanism can reside inside or outside of computer 135 and can include an x-ray controller that provides power and timing signals to x-ray source 105 and any gantry motor controller that controls the rotational speed and position of gantry 110. A data acquisition system in the control mechanism can sample analog data from detector elements 130 and convert the data to digital signals for subsequent processing. In some embodiments, these digital signals can be stored in a system data store (SDS) described in further detail below. An image reconstructor using the methods described in attachments 1 and 2 can receive sampled and digitized x-ray data from the data acquisition system and perform image reconstruction. The reconstructed image can be applied as an input to a system data store or system processor, as further described hereinbelow, or computer 135.

In one embodiment, computer 135 can also receive commands and scanning parameters from an operator via console that has a keyboard. An associated cathode ray tube display 135D, or other suitable display device (e.g., liquid crystal display, plasma display, etc.), can be used to allow the operator to observe the reconstructed image and other data from computer 135. The operator supplied commands and parameters are used by computer 135 to provide control signals and information to data acquisition system, x-ray controller and gantry motor controller.

According to an exemplary embodiment, the image processing and reconstruction system includes a system processor potentially including multiple processing elements.

The term processing element may refer to (1) a process running on a particular piece, or across particular pieces, of processing hardware, (2) a particular piece of processing hardware, or either (1) or (2) as the context allows. Each processing element can be supported via a standard general purpose processor such as the processor within the Silicon Graphics O2 computing platform discussed hereinabove; alternative processors such as UltraSPARC (Sun Microsystems, Palo Alto, Calif.) or an Intel-compatible processor platforms preferably using at least one PENTIUM III, PENTIUM IV or CELERON (Intel Corp., Santa Clara, Calif.) class processor could be used in other embodiments. The system processor can include one or more field programmable gate arrays (FPGAs) and/or application specific integrated circuits (ASICs) configured to perform at least a portion of the functionality according to the present invention. In some embodiments, the system processor can include a combination of general purpose processors, ASICs and/or FPGAs. In some embodiments, image processing and reconstruction, as further described in attachments 1 and 2, can be distributed across multiple processing elements. In some such embodiments, aspects of the functionality, or portions thereof, may be executed in series or in parallel; particular functionality, or portions thereof, executed a multiplicity of times may also occur in series or parallel. In FIG. 1, computer 135, or portions thereof, can be included within, or serve as, the system processor of the present invention.

In a system processor including at least one general purpose processor, the general purpose processor typically runs an appropriate operating system such as WINDOWS/NT, WINDOWS 2000 or WINDOWS/XP (Microsoft, Redmond, Wash.), Solaris (Sun Microsystems, Palo Alto, Calif.), or LINUX (or other UNIX variant). In some embodiments that include the Silicon Graphics O2 platform discussed hereinabove, the operating system used is Silicon Graphics' UNIX variant.

The SDS referenced above may include a variety of primary and secondary storage elements. In one embodiment, the SDS may include RAM as part of the primary storage; the amount of RAM might range, for example, from 256 MB to 2 GB in embodiments including a computer workstation. One skilled in the art will recognize that depending on the image resolution, the amount of storage used can vary significantly. The primary storage can in some embodiments include other forms of memory such as cache memory, registers, non-volatile memory (e.g., FLASH, ROM, EPROM, etc.), etc.

The SDS can also include secondary storage including single, multiple and/or varied servers and storage elements. For example, the SDS may use internal storage devices connected to the system processor. In embodiments where a single processing element supports all of the system functionality, such as computer 135 in FIG. 1, a local hard disk drive can serve as the secondary storage of the SDS, and a disk operating system executing on such a single processing element can act as a data server receiving and servicing data requests. A system bus would serve as the communication channel between the system processor and the SDS (typically, at least RAM and the hard disk drive).

It will be understood by those skilled in the art that the different information used in the analysis and control processes and systems according to the present invention can be logically or physically segregated within a single device serving as secondary storage for the SDS; multiple related data stores accessible through a unified management system, which together serve as the SDS; or multiple independent data stores individually accessible through disparate management systems, which may in some embodiments be collectively viewed as the SDS. The various storage elements that comprise the physical architecture of the SDS may be centrally located, or distributed across a variety of diverse locations.

The architecture of the secondary storage of the system data store may vary significantly in different embodiments. In several embodiments, database(s) are used to store and manipulate the data; in some such embodiments, one or more relational database management systems, such as DB2 (IBM, White Plains, N.Y.), SQL Server (Microsoft, Redmond, Wash.), ACCESS (Microsoft, Redmond, Wash.), ORACLE 8i (Oracle Corp., Redwood Shores, Calif.), Ingres (Computer Associates, Islandia, N.Y.), MySQL (MySQL AB, Sweden) or Adaptive Server Enterprise (Sybase Inc., Emeryville, Calif.), may be used in connection with a variety of storage devices/file servers that may include one or more standard magnetic and/or optical disk drives using any appropriate interface including, without limitation, IDE and SCSI. In some embodiments, a tape library such as Exabyte X80 (Exabyte Corporation, Boulder, Colo.), a storage attached network (SAN) solution such as available from (EMC, Inc., Hopkinton, Mass.), a network attached storage (NAS) solution such as a NetApp Filer 740 (Network Appliances, Sunnyvale, Calif.), or combinations thereof may be used. In other embodiments, the data store may use database systems with other architectures such as object-oriented, spatial, object-relational or hierarchical.

Instead of, or in addition to, those organization approaches discussed above, certain embodiments may use other storage implementations such as hash tables or flat files or combinations of such architectures. Such alternative approaches may use data servers other than database management systems such as a hash table look-up server, procedure and/or process and/or a flat file retrieval server, procedure and/or process. Further, the SDS may use a combination of any of such approaches in organizing its secondary storage architecture.

The SDS communicates with the system processor by one or more communication channels. Multiple channels can be involved in some embodiments for supporting communication between processing elements of the system processor and portions of the SDS. Such channels can include without limitation computer network, direct dial-up connection, dedicated connection, direct or indirect connection such as via a bus connection, parallel or serial connection, USB connection, null modem connection or wireless connection utilizing an appropriate communication protocol such as BLUETOOTH, IRDA, 802.11b or other suitable channel as would be known to those skilled in the art.

All forms of data, including raw, intermediate, and computed can be stored on one or more SDS either temporarily or permanently.

In one embodiment, a Grangeat-type half-scan algorithm is used in the circular scanning case. In another embodiment, the Grangeat-type half-scan algorithm is extended to work in a helical case without data truncation. In yet another embodiment, the Grangeat-type half-scan algorithm is extended to work in a helical case with data truncation. These embodiments are described in further detail below.

A Grangeat-Type Half-Scan Algorithm for Cone-Beam CT

According to a first exemplary embodiment, a Grangeat-type half-scan algorithm is provided in the circular scanning case. Appropriate data filling is performed using the Grangeat approach, and the off-mid-plane artifacts associated algorithms, such as the Feldkamp-type algorithms, are suppressed.

In the following, Grangeat's formula for circular half-scan geometry is modified by combining redundant data to improve contrast resolution while optimizing temporal resolution. The redundant data are weighted with smooth functions to suppress data inconsistence.

Figure 2:
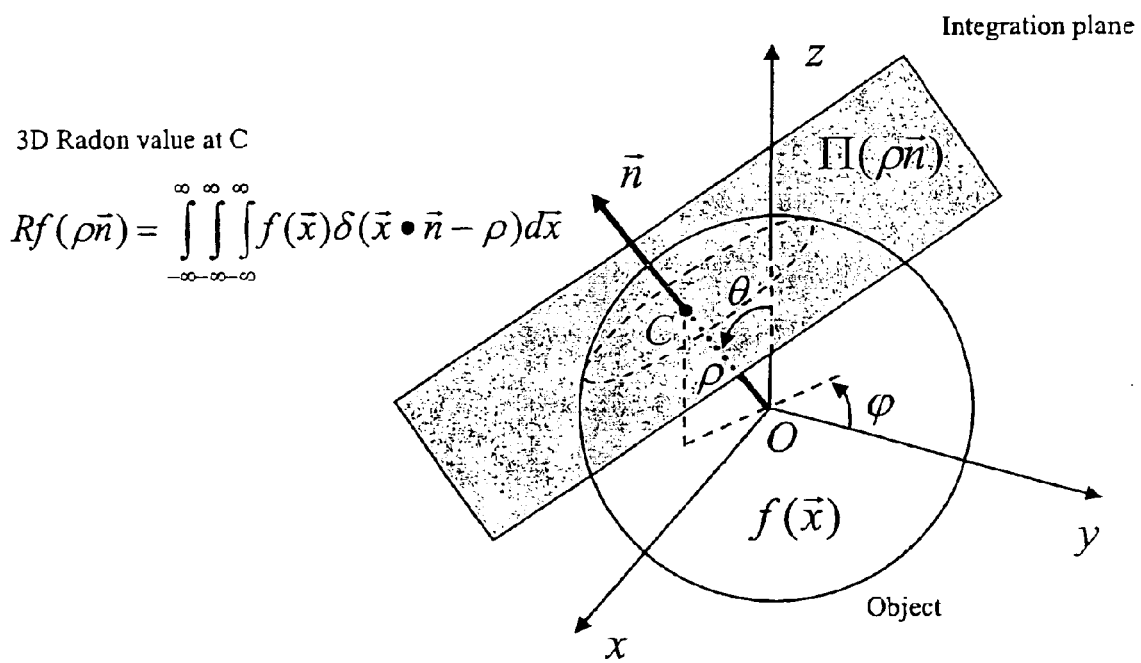
FIG. 2 illustrates exemplary cone beam geometry and plane integration which is equivalent to a 3 Radon transform according to exemplary embodiments.

As shown in FIG. 2, the Radon transform of a 3D-function $f(\vec{x})$ is defined by $$Rf(\rho\vec{n}) = \int_{-\infty}^{\infty}\int_{-\infty}^{\infty}\int_{-\infty}^{\infty} f(\vec{x})\delta(\vec{x}\cdot\vec{n} - \rho)d\vec{x} \quad (1)$$

where $\vec{n}$ is the unit vector which passes through the characteristic point C described by spherical coordinates $(\rho,\theta,\phi)$, $\vec{x}$ Cartesian coordinates $(x, y, z)$. Eq. (1) means that the Radon value at C is the integral of the object function $f(\vec{x})$ on the plane through C and normal to the vector $\vec{n}$. It is well known that the 3-D function $f(\vec{x})$ can be reconstructed from $Rf(\rho\vec{n})$ provided that $Rf(\rho\vec{n})$ is available for all planes through a neighborhood of point $\vec{x}$. The inversion formula of the 3D Radon transform is given by $$f(\vec{x}) = \frac{-1}{8\pi^2}\int_{\theta=-\pi/2}^{\pi/2}\int_{\varphi=0}^{2\pi}\frac{\partial^2}{\partial\rho^2}Rf[(\vec{x}\cdot\vec{n})\vec{n}]|\sin\theta|d\varphi d\theta \quad (2)$$

For cone-beam CT, it is instrumental to connect cone-beam data to 3D Radon data. One connection is Grangeat's formulation, which is geometrically attractive.

Figure 3A:
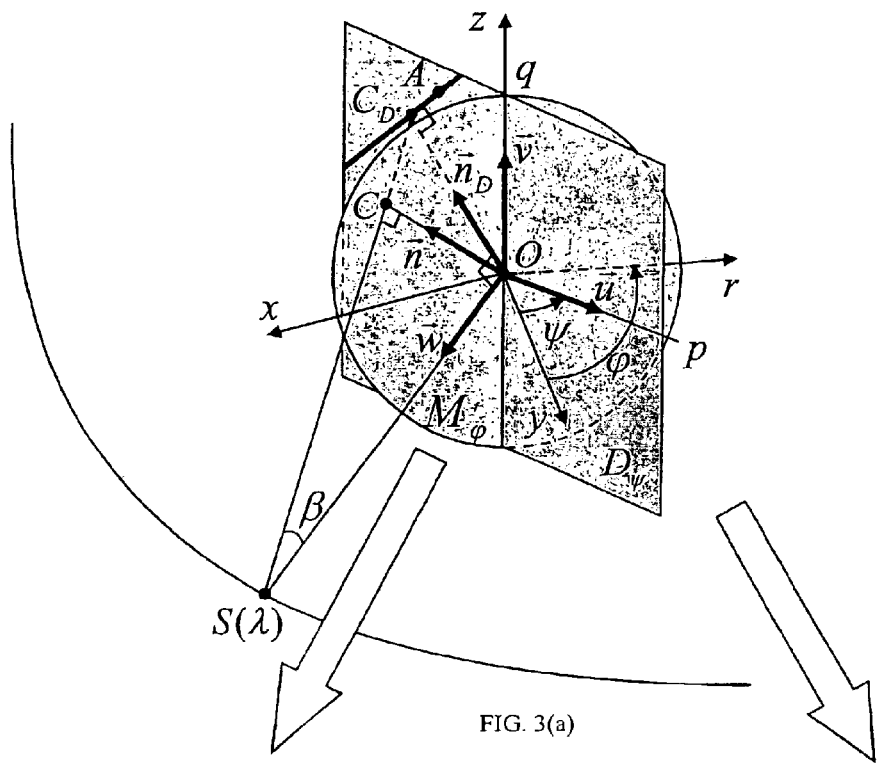
FIGS. 3($a$)–($c$) illustrate exemplary meridian and detector planes for a circular scan.
Figure 3B:
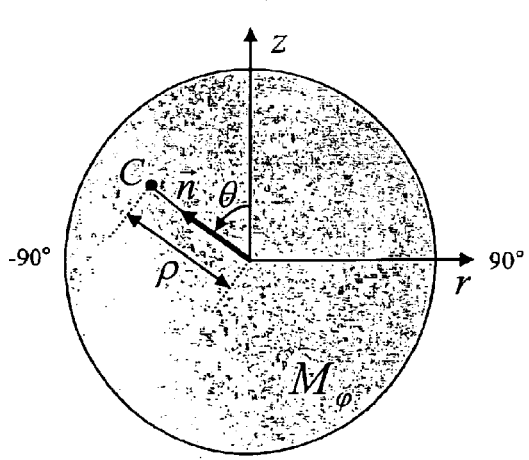

Mathematically, as shown in FIG. 3, the link can be expressed as follows:

$$\frac{\partial}{\partial\rho}Rf(\rho\vec{n}) = R'f(\rho\vec{n}) \quad (3)$$

$$= \frac{1}{\cos^2\beta}\frac{\partial}{\partial s}\int_{-\infty}^{\infty}\frac{SO}{SA}Xf[s(\rho\vec{n}), t, \psi(\rho\vec{n})]dt$$

$$= \frac{1}{\cos^2\beta}\frac{\partial}{\partial s}\int_{-\infty}^{\infty}X_wf[s(\rho\vec{n}), t, \psi(\rho\vec{n})]dt,$$

where $X_f[s(\rho\vec{n}),t,\psi(\rho\vec{n})]$ is the detector value the distance $s$ away from the detector center O along the line t perpendicular to $OC_D$ on the detector plane $D_\psi$ located at the angle $\psi$ from the y-axis, $SO$ denotes the distance between the source and the origin, $SA$ the distance between the source and an arbitrary point A along $t$, and $\beta$ denotes the angle between the line SO and SC, and $$X_wf[s(\rho\vec{n}), t, \psi(\rho\vec{n})] = \frac{SO}{SA}Xf[s(\rho\vec{n}), t, \psi(\rho\vec{n})].$$

Given a characteristic point $C$ in the Radon domain, the plane orthogonal to the vector $\rho\vec{n}$ is determined. Then, the intersection point(s) of the plane with the source trajectory $S(\lambda)$ can be found, and the detector plane(s) $D_\psi$ specified, on which the line integration can be performed. Let $C_D$ denote the intersection of the detector plane $D_\psi$ with the ray that comes from $S(\lambda)$ and goes through $C$. The position $C_D$ can be described by a vector $s\vec{n}_D$. To compute the derivative of Radon value at $C$, the line integration is performed along $t$, which is orthogonal to the vector $s\vec{n}_D$.

Figure 3C:
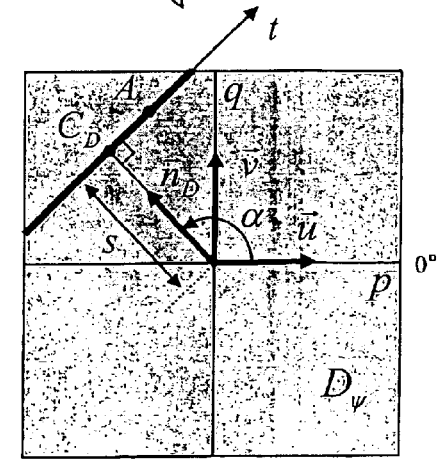

For a digital implementation of Eq. (3), the derivative in the s-direction is reformulated as the sum of its horizontal and vertical components as Eq. (4) below:

$$\frac{\partial}{\partial s}X_wf[s(\rho\vec{n}), t, \psi(\rho\vec{n})] = \cos[\alpha(\rho\vec{n})]\frac{\partial}{\partial p}X_wf[s(\rho\vec{n}), t, \psi(\rho\vec{n})] +$$

$$\sin[\alpha(\rho\vec{n})]\frac{\partial}{\partial q}X_wf[s(\rho\vec{n}), t, \psi(\rho\vec{n})]$$

where p and q are the Cartesian axes, s and $\alpha$ define a polar system on the detector plane (See FIG. 3(c)). Substituting Eq. (4) into Eq. (3), we have Eq. (5) as follows:

$$R'f(\rho\vec{n}) = \frac{1}{\cos^2\beta}\bigg(\cos[\alpha(\rho\vec{n})]\int_{-\infty}^{\infty}\frac{\partial}{\partial p}X_wf[s(\rho\vec{n}), t, \psi(\rho\vec{n})]dt +$$

$$\sin[\alpha(\rho\vec{n})]\int_{-\infty}^{\infty}\frac{\partial}{\partial q}X_wf[s(\rho\vec{n}), t, \psi(\rho\vec{n})]dt\bigg)$$

where $\cos\beta = \frac{SO}{SC_D}$.

Grangeat-Type Half-Scan Formula

Eq. (3) can be modified into the following half-scan version.

$$\frac{\partial}{\partial\rho}Rf(\rho\vec{n}) = \sum_{i=1}^{2}\omega_i(\rho\vec{n})\frac{1}{\cos^2\beta}\frac{\partial}{\partial s}\int_{-\infty}^{\infty}\frac{SO}{SA}Xf(s(\rho\vec{n}), t, \psi_i(\rho\vec{n}))dt \quad (6)$$

where $$\psi_1(\rho, \theta, \varphi) = \varphi + \sin^{-1}\left[\frac{\rho}{SO\sin\theta}\right] \quad (7)$$

$$\psi_2(\rho, \theta, \varphi) = \varphi + \pi - \sin^{-1}\left[\frac{\rho}{SO\sin\theta}\right] \quad (8)$$

and $\omega_1(\rho,\theta,\phi)$ and $\omega_2(\rho,\theta,\phi)$ are smooth weighting functions explained in detail below.

A derivation of the Grangeat-type half-scan algorithm follows.

Derivation of the Grangeat-type Half-scan Algorithm

As indicated above, Grangeat found a link between Radon data and cone-beam projection data, which is expressed as follows.

$$\frac{\partial}{\partial\rho}Rf(\rho\vec{n}) = R'f(\rho\vec{n}) \quad (a1)$$

$$= \frac{1}{\cos^2\beta}\frac{\partial}{\partial s}\int_{-\infty}^{\infty}\frac{SO}{SA}Xf[s(\rho\vec{n}), t, \psi(\rho\vec{n})]dt$$

$$= \frac{1}{\cos^2\beta}\frac{\partial}{\partial s}\int_{-\infty}^{\infty}X_wf[s(\rho\vec{n}), t, \psi(\rho\vec{n})]dt$$

In the circular full-scan case, there always exist two detector planes from which the Radon data can be calculated except for the shadow zone. The detector planes are specified by the following two equations:

$$\psi_1(\rho, \theta, \varphi) = \varphi + \sin^{-1}\left[\frac{\rho}{SO\sin\theta}\right], \quad (a2)$$

$$\psi_2(\rho, \theta, \varphi) = \varphi + \pi - \sin^{-1}\left[\frac{\rho}{SO\sin\theta}\right]. \quad (a3)$$

In an ideal situation where data is noise-free and the object is stationary during the rotation, we have Eq. (a4) which follows:

$$\frac{1}{\cos^2\beta}\frac{\partial}{\partial s}\int_{-\infty}^{\infty}\frac{SO}{SA}X_w f(s(\vec{\rho n}), t, \psi_1(\vec{\rho n}))dt =$$

$$\frac{1}{\cos^2\beta}\frac{\partial}{\partial s}\int_{-\infty}^{\infty}\frac{SO}{SA}X_w f(s(\vec{\rho n}), t, \psi_2(\vec{\rho n}))dt$$

Therefore, the radon data can be calculated from either of the detector planes. However, in practice we should consider the following practical conditions: (1) Projection data contain noise; (2) Data from $D_{\psi_1}$ and $D_{\psi_2}$ may be different due to motion of an object.

Hence, we have:

$$\frac{1}{\cos^2\beta}\frac{\partial}{\partial s}\int_{-\infty}^{\infty}\frac{SO}{SA}Xf(s(\vec{\rho n}), t, \psi_1(\vec{\rho n}))dt \neq \quad (a5)$$

$$\frac{1}{\cos^2\beta}\frac{\partial}{\partial s}\int_{-\infty}^{\infty}\frac{SO}{SA}Xf(s(\vec{\rho n}), t, \psi_2(\vec{\rho n}))dt$$

Considering noise in projection data, we should combine redundant data to improve the signal-to-noise ratio. Consequently, Eq. (a5) can be modified to the following:

$$\frac{\partial}{\partial \rho}Rf(\vec{\rho n}) = \sum_{i=1}^{2}\omega_i(\vec{\rho n})\frac{1}{\cos^2\beta}\frac{\partial}{\partial s}\int_{-\infty}^{\infty}\frac{SO}{SA}Xf(s(\vec{\rho n}), t, \psi_i(\vec{\rho n}))dt, \quad (a6)$$

where $\omega_1(\rho\vec{n})+\omega_2(\rho\vec{n})=1$. To maximize the signal to noise ratio, both $\omega_1(\rho\vec{n})$ and $\omega_2(\rho\vec{n})$ should equal to ½.

However, when motion is significant, one of the solutions to suppress the motion artifacts is to use half-scan, which is an important goal according to exemplary embodiments. But in this case, data are not always redundant by a factor of two. More exactly, there are generally doubly, singly sampled regions, and shadow zones on a meridian plane. Therefore, there exist discontinuities between the adjacent regions. Hence, the smooth weighting functions such as those described below are needed to suppress the associated artifacts.

Figure 4:
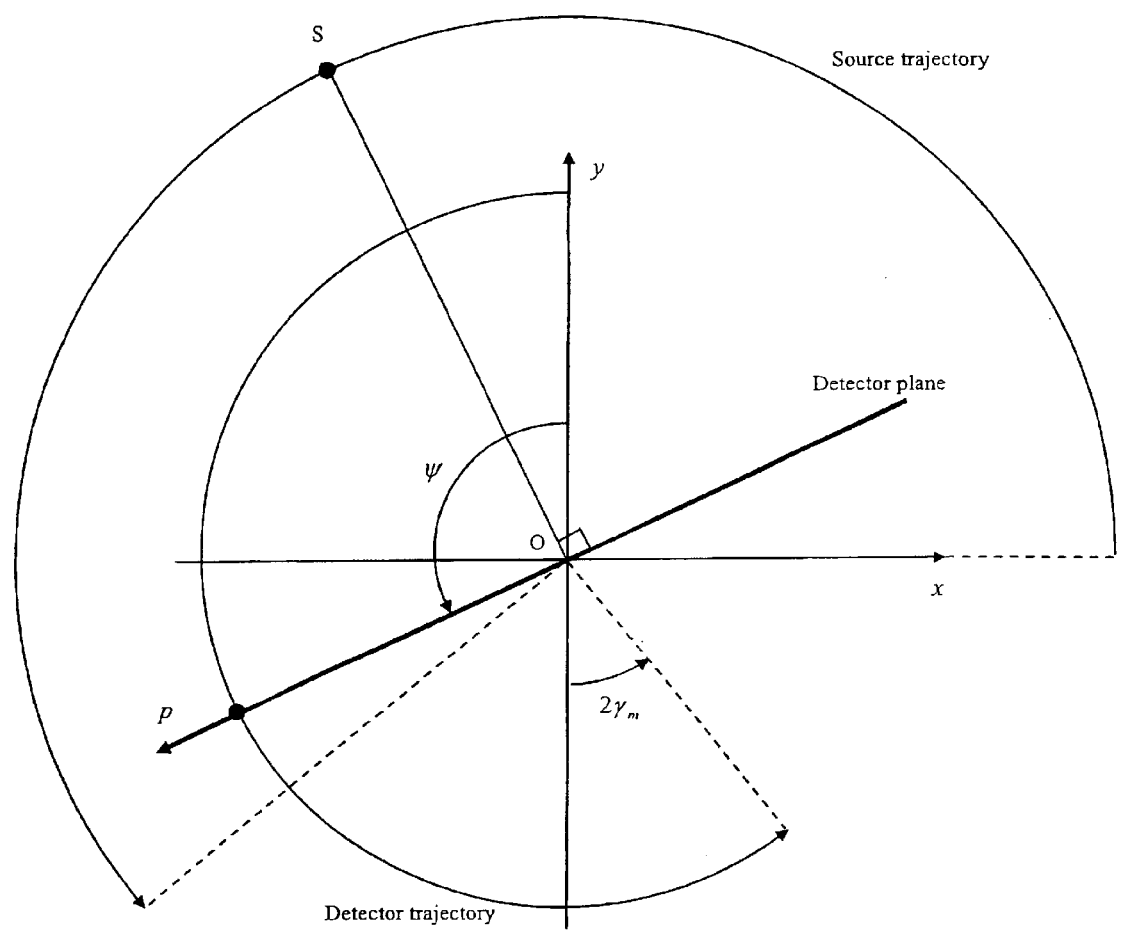
FIG. 4 illustrates exemplary half-scan geometry as it relates to a first embodiment.
Figure 5A:
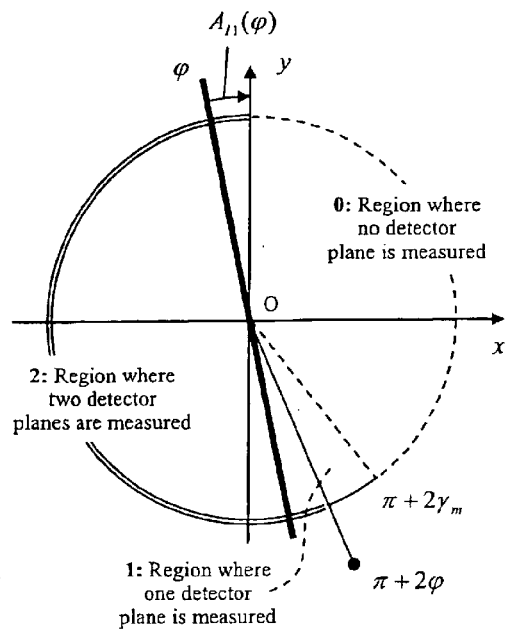
FIGS. 5($a$)–($d$) illustrate a number of exemplary measured detector planes and critical angles in the four angular intervals I1, I2, I3, and I4, respectively.
Figure 5B:
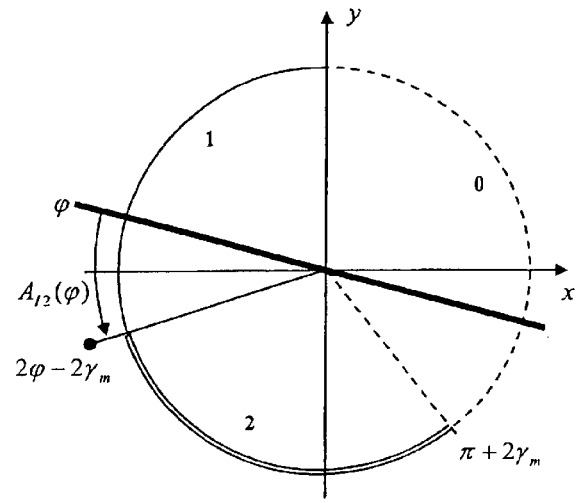
Figure 5C:
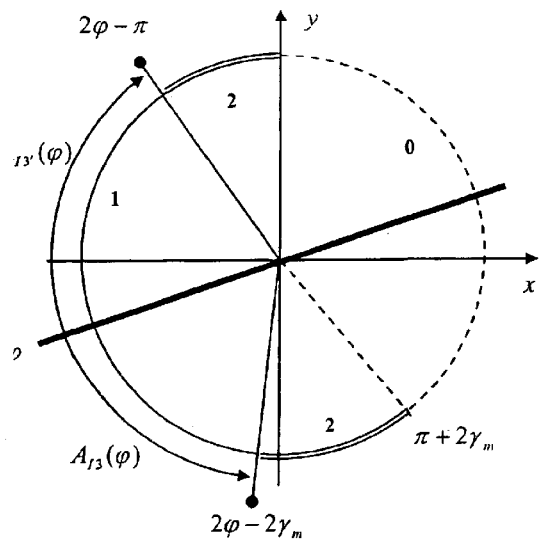
Figure 5D:
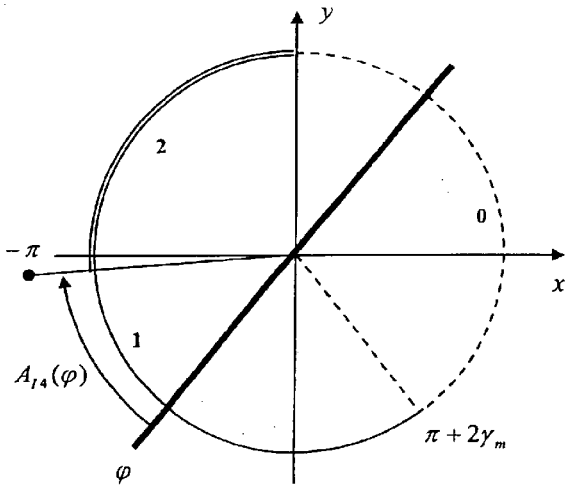

Exemplary half-scan geometry is depicted in FIG. 4, which is the central plane where the source trajectory resides. The cone angle is denoted as $\gamma_m$, defined as a half of the full cone-angle. The scanning angle $\psi$ varies from 0 to $\pi+2\gamma_m$. The horizontal axis of a detector plane is denoted as p.

In the circular full-scan case, for any characteristic point not in the shadow zone or on its surface there exist a pair of detector planes specified by Eqs. (7) and (8). However, in the circular half-scan case, the dual planes are not always available. When the dual planes are found, we are in a "doubly sampled zone"; when one of them is missing due to the half-scan, we are in a "singly sampled zone". Of course, there is not an associated detector plane in the shadow zone. Relative to the full-scan, the shadow zone is increased due to the half-scan. The shadow zone area on a meridian plane depends on the angle $\phi$ of the meridian plane.

Boundaries Between Singly and Doubly Sampled Zones

The boundary equations between these zones are instrumental for design of weighing functions $\omega_1(\rho,\theta,\phi)$ and $\omega_2(\rho,\theta,\phi)$, as well as interpolation and extrapolation into the shadow zone. The term $$\sin^{-1}\left[\frac{\rho}{SO\sin\theta}\right]$$

in Eqs. (7) and (8) is the angular difference between the meridian plane $M_\phi$ and the detector plane $D_\psi$, where the line integration is performed. This angular difference ranges from −90 to +90 degrees. Given a half-scan range and a meridian angle $\phi$, it can be determined whether $D_{\psi_1}$ and $D_{\psi_2}$ are available by evaluating $$\sin^{-1}\left[\frac{\rho}{SO\sin\theta}\right].$$

It is emphasized that the following geometric property is important to understand the relationship between singly and doubly sampled zones. For a given characteristic point, the normal directions of the two associated detector planes must be symmetric to the normal direction of the meridian plane containing that characteristic point.

Denoting $A(\phi)$ as the critical angle which separates the singly and doubly sampled zones, as shown in FIGS. 5(a)–(d), then the number of the available detector planes changes from two to one or one to two across this critical angle. Specifically, for the meridian plane of an angle $\phi$ the boundary between the singly and doubly sampled zones is expressed as $$\sin^{-1}\left[\frac{\rho_b}{SO\sin\theta}\right] = A(\varphi).$$

Therefore, we have $$\rho_b(\theta,\phi)=SO\sin A(\phi)\sin\theta. \quad (9)$$

The critical angle function $A(\phi)$ takes different forms depending on the meridian angle $\phi$. We have the following four intervals:

I1: $0\leq\phi<\gamma_m$,

I2: $\gamma_m\leq\phi<90$,

I3: $90\leq\phi<90+2\gamma_m$,

I4: $90+2\gamma_m\leq\phi<180$. (10)

If a pair of detector planes, $D_{\phi+A(\phi)}$ and $D_{\pi+\phi-A(\phi)}$, are available, there exist two redundant data for $(\rho,\theta,\phi)$. If only either of them is available, there exists only one data. If none of them is available, there exists no data. In FIGS. 5(a)–(d), the availability of $D_{\phi+A(\phi)}$ and $D_{\pi+\phi-A(\phi)}$ are marked showing whether both are available, only either of them available, or none of them available for a given meridian plane $M_\phi$. There are the four intervals in FIGS. 5(a)–(d). For I1, both $D_{\phi+A(\phi)}$ and $D_{\pi+\phi-A(\phi)}$ are available when $-\phi\leq A(\phi)\leq\pi/2$. Only $D_{\pi+\phi-A(\phi)}$ is available when $2\gamma_m-\phi\leq A(\phi)<-\phi$. Therefore, the boundary between doubly and singly region is formed at $A_{I1}(\phi)=-\phi$. Hence, boundary equation becomes $\rho_b(\theta,\phi)=SO\sin(-\phi)\sin\theta$ from Eq. 9. In the same manner, the critical angle functions can be acquired for the other intervals and are expressed as follows:

I1: $A_{I1}(\phi)=-\phi$,

I2: $A_{I2}(\phi)=\phi-2\gamma_m$,

I3: $A_{I3}(\phi)=\phi-2\gamma_m$, and $A_{I3'}(\phi)=\phi-\pi$,

I4: $A_{I4}(\phi)=\phi-\pi$. (10)

Figure 6:
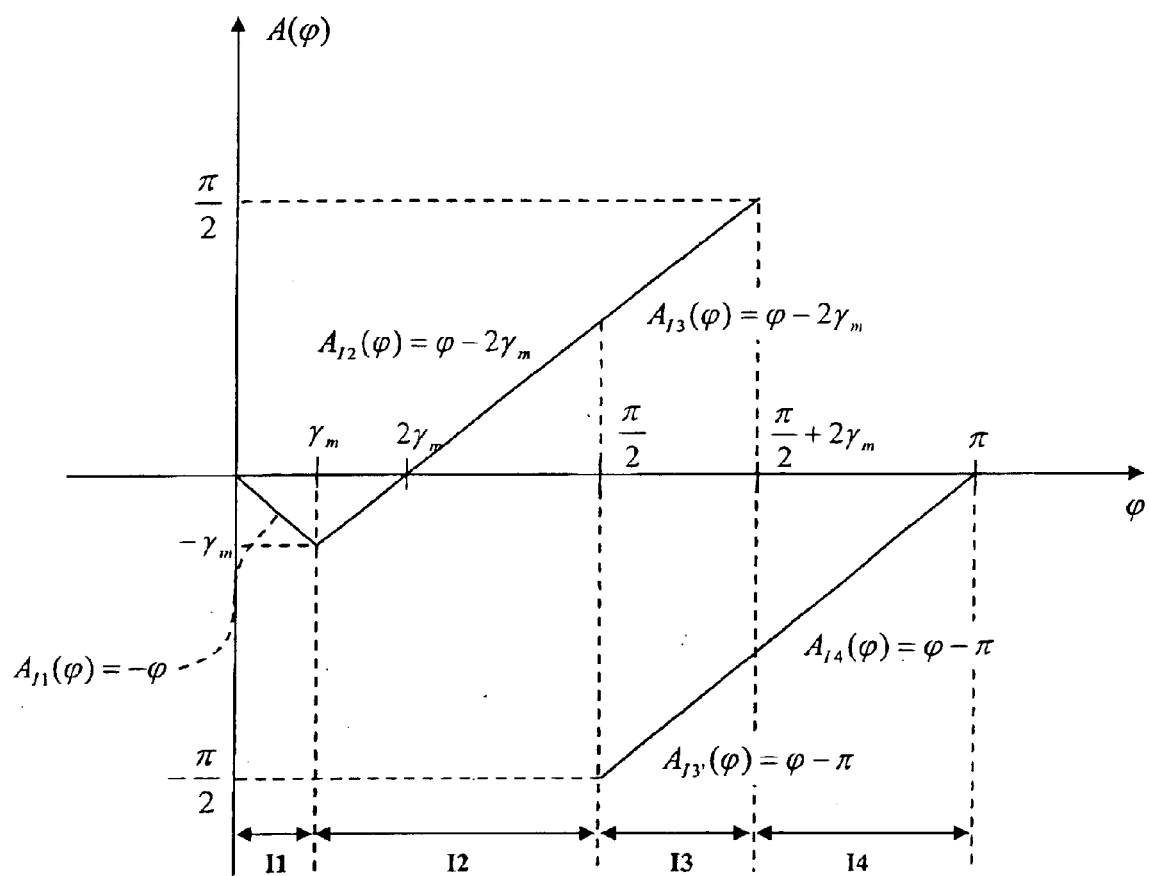
FIG. 6 illustrates exemplary plots of the critical angle functions.

These critical angle functions are plotted in FIG. 6. It should be noted that there exist two critical functions for I3. Therefore, there exist two boundaries in this interval, given as $\rho_b(\theta,\phi)=SO\sin(A_{I3}(\phi))\sin\theta$ and $\rho_b'(\theta,\phi)=SO\sin(A_{I3}(\phi))\sin\theta$, respectively.

Shadow Zone Boundaries

The shadow zone boundaries are needed to interpolate/extrapolate for missing data. The boundary equation for the shadow zone in the full-scan case is given by $$\rho_s = SO\sin(\theta) \tag{12}$$

Figure 7A:
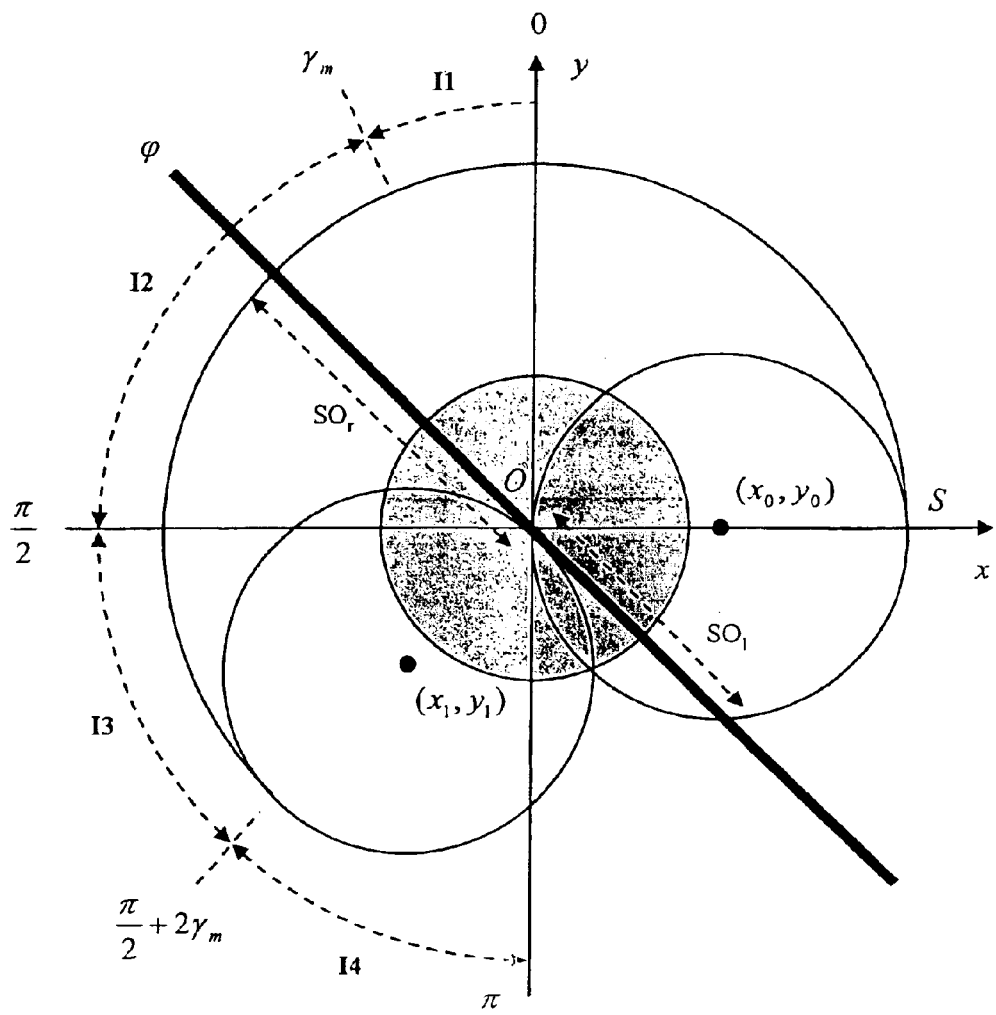
FIGS. 7($a$) and 7($b$) illustrate exemplary shadow zone geometry for a mid-plane view and a meridian plane view, respectively.
Figure 7B:
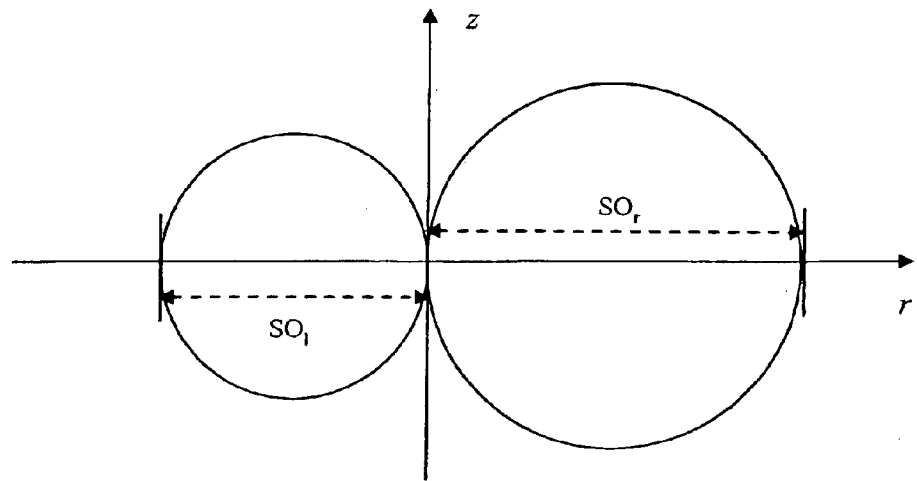
Figure 8A:
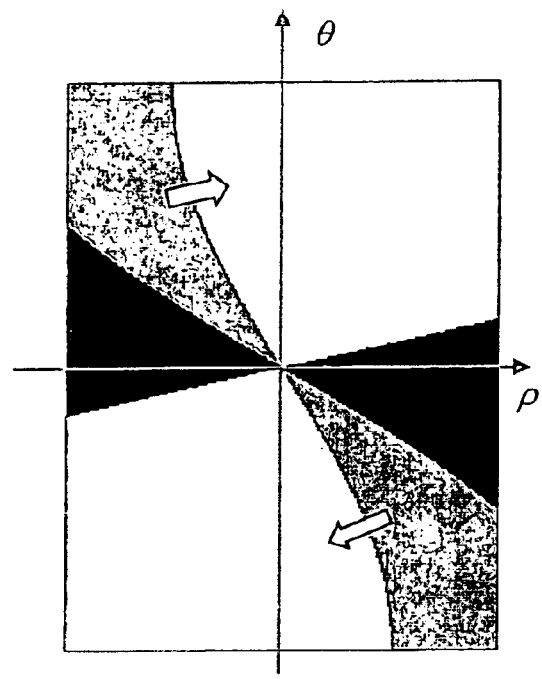
FIGS. 8($a$)–8($d$) illustrate exemplary maps of singly and doubly sampled zones, as well as shadow zones on different meridian planes. The angles represented in FIGS. 8($a$)–8($d$) are 7, 40, 103, and 170 degrees, respectively.
Figure 8B:
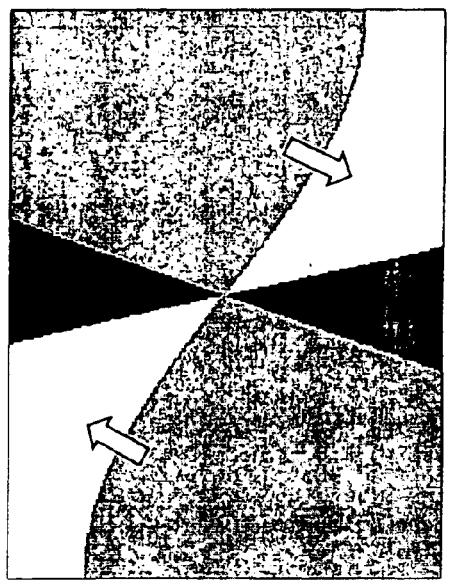
Figure 8C:
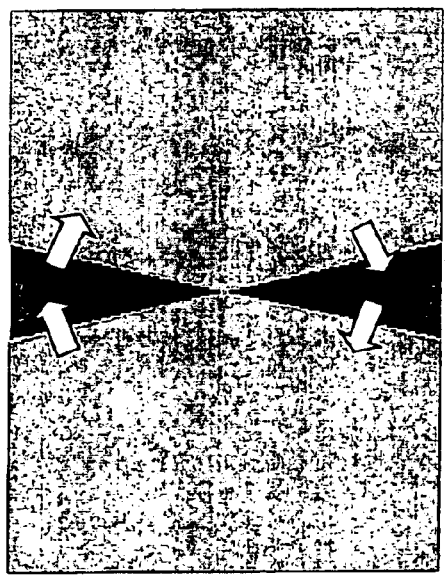
Figure 8D:
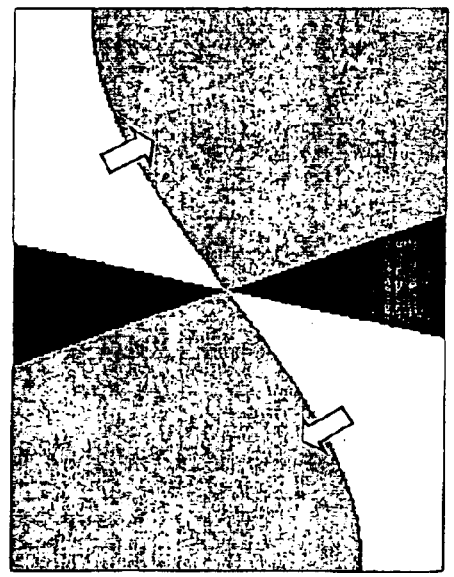

In other words, each detector plane gives a Radon circle of diameter SO on the meridian plane. However, in the half-scan case, the diameter of the Radon circle may change, depending on the meridian plane angle, as shown in FIGS. 7(a)–(b). Specifically, given a meridian plane, we can find both the diameters of the two Radon circles on the plane. Then, we can express the shadow zone boundaries as follows:

$$\rho_s = SO_l(\phi)\sin(\theta),\ \rho\theta<0,$$
$$\rho_s = SO_r(\phi)\sin(\theta),\ \rho\theta\geq 0. \tag{13}$$

In reference to FIGS. 7(a)–(b), it is easy to verify that $$x_0 = SO/2, y_0 = 0$$
$$x_1 = (SO/2)\cos(2\gamma_m+\pi),$$
$$y_1 = (SO/2)\sin(2\gamma_m+\pi). \tag{14}$$

Then, it can be geometrically derived in each of the four intervals that $$\text{I1: } SO_l(\varphi) = \frac{|2x_1 - 2y_1\cot\varphi|}{|\cos ec\varphi|},\ SO_r(\varphi) = SO; \tag{15}$$

$$\text{I2: } SO_l(\varphi) = \frac{|2x_0 - 2y_0\cot\varphi|}{|\cos ec\varphi|},\ SO_r(\varphi) = SO;$$

$$\text{I3: } SO_l(\varphi) = SO,\ SO_r(\varphi) = SO;$$

$$\text{I4: } SO_l(\varphi) = SO,\ SO_r(\varphi) = \frac{|2x_1 - 2y_1\cot\varphi|}{|\cos ec\varphi|}.$$

Weighting Functions

Using the above boundary equations, we can graphically depict the singly and doubly sampled zones, along with the shadow zones. Four maps from different meridian planes are represented in FIGS. 8(a)–(d). White area stands for the doubly sampled region, gray for the singly sampled region, and black for the shadow zone. When data are consistent, we can set $$\omega_1 = \omega_2 = \frac{1}{2}$$

for the doubly sampled region, set the valid one to 1 and the other as 0 for the singly sampled region, and set both to zero for the shadow zone where missing data will be estimated afterwards. When data are inconsistent in practice, the following smooth weighting functions are designed according to Parker's half-scan weighting scheme:

I1:

$$\omega_1(\rho,\theta,\varphi) = \begin{cases} \cos^2\left(\frac{\pi}{2}\frac{\rho-(-\delta)}{\rho_b(\theta)-(-\delta)}\right), & \theta<0, \rho<\rho_b(\theta); \\ 0, & \theta<0, \rho\geq\rho_b(\theta); \\ 0, & \theta\geq 0, \rho<\rho_b(\theta); \\ \sin^2\left(\frac{\pi}{2}\frac{\rho-\rho_b(\theta)}{\delta-\rho_b(\theta)}\right), & \theta\geq 0, \rho\geq\rho_b(\theta). \end{cases} \tag{16}$$

$$\omega_2(\rho,\theta,\varphi) = \begin{cases} \sin^2\left(\frac{\pi}{2}\frac{\rho-(-\delta)}{\rho_b(\theta)-(-\delta)}\right), & \theta<0, \rho<\rho_b(\theta); \\ 1, & \theta<0, \rho\geq\rho_b(\theta); \\ 1, & \theta\geq 0, \rho<\rho_b(\theta); \\ \cos^2\left(\frac{\pi}{2}\frac{\rho-\rho_b(\theta)}{\delta-\rho_b(\theta)}\right), & \theta\geq 0, \rho\geq\rho_b(\theta). \end{cases} \tag{17}$$

I2:

$$\omega_1(\rho,\theta,\varphi) = \begin{cases} \sin^2\left(\frac{\pi}{2}\frac{\rho-(-\delta)}{\rho_b(\theta)-(-\delta)}\right), & \theta<0, \rho<\rho_b(\theta); \\ 1, & \theta<0, \rho\geq\rho_b(\theta); \\ 1, & \theta\geq 0, \rho<\rho_b(\theta); \\ \cos^2\left(\frac{\pi}{2}\frac{\rho-\rho_b(\theta)}{\delta-\rho_b(\theta)}\right), & \theta\geq 0, \rho\geq\rho_b(\theta). \end{cases} \tag{18}$$

$$\omega_2(\rho,\theta,\varphi) = \begin{cases} \cos^2\left(\frac{\pi}{2}\frac{\rho-(-\delta)}{\rho_b(\theta)-(-\delta)}\right), & \theta<0, \rho<\rho_b(\theta); \\ 0, & \theta<0, \rho\geq\rho_b(\theta); \\ 0, & \theta\geq 0, \rho<\rho_b(\theta); \\ \sin^2\left(\frac{\pi}{2}\frac{\rho-\rho_b(\theta)}{\delta-\rho_b(\theta)}\right), & \theta\geq 0, \rho\geq\rho_b(\theta). \end{cases} \tag{19}$$

I3:

$$\omega_1(\rho,\theta,\varphi) = \begin{cases} \sin^2\left(\frac{\pi}{2}\frac{\rho-(-\delta)}{\rho_b(\theta)-(-\delta)}\right), & \theta<0, \rho<\rho_b(\theta); \\ 1, & \theta<0, \rho_b(\theta)\leq\rho<\rho_b'(\theta); \\ \cos^2\left(\frac{\pi}{2}\frac{\rho-\rho_b'(\theta)}{\delta-\rho_b'(\theta)}\right), & \theta<0, \rho\geq\rho_b'(\theta); \\ \sin^2\left(\frac{\pi}{2}\frac{\rho-(-\delta)}{\rho_b'(\theta)-(-\delta)}\right), & \theta\geq 0, \rho<\rho_b'(\theta); \\ 1, & \theta\geq 0, \rho_b'(\theta)\leq\rho<\rho_b(\theta); \\ \cos^2\left(\frac{\pi}{2}\frac{\rho-\rho_b(\theta)}{\delta-\rho_b(\theta)}\right), & \theta\geq 0, \rho\geq\rho_b(\theta). \end{cases} \tag{20}$$

$$\omega_2(\rho,\theta,\varphi) = \begin{cases} \cos^2\left(\frac{\pi}{2}\frac{\rho-(-\delta)}{\rho_b(\theta)-(-\delta)}\right), & \theta<0, \rho<\rho_b(\theta); \\ 0, & \theta<0, \rho_b(\theta)\leq\rho<\rho_b'(\theta); \\ \sin^2\left(\frac{\pi}{2}\frac{\rho-\rho_b'(\theta)}{\delta-\rho_b'(\theta)}\right), & \theta<0, \rho\geq\rho_b'(\theta); \\ \cos^2\left(\frac{\pi}{2}\frac{\rho-(-\delta)}{\rho_b'(\theta)-(-\delta)}\right), & \theta\geq 0, \rho<\rho_b'(\theta); \\ 0, & \theta\geq 0, \rho_b'(\theta)\leq\rho<\rho_b(\theta); \end{cases} \tag{21}$$

-continued $$\sin^2\left(\frac{\pi}{2}\frac{\rho-\rho_b(\theta)}{\delta-\rho_b(\theta)}\right), \quad \theta \geq 0, \rho \geq \rho_b(\theta).$$

I4:

$$\omega_1(\rho, \theta, \varphi) = 1, \quad \theta < 0, \rho < \rho_b(\theta); \quad (22)$$

$$\cos^2\left(\frac{\pi}{2}\frac{\rho-\rho_b(\theta)}{\delta-\rho_b(\theta)}\right), \quad \theta < 0, \rho \geq \rho_b(\theta);$$

$$\sin^2\left(\frac{\pi}{2}\frac{\rho-(-\delta)}{\rho_b(\theta)-(-\delta)}\right), \quad \theta \geq 0, \rho < \rho_b(\theta);$$

$$1, \quad \theta \geq 0, \rho \geq \rho_b(\theta).$$

$$\omega_2(\rho, \theta, \varphi) = 0, \quad \theta < 0, \rho < \rho_b(\theta); \quad (23)$$

$$\sin^2\left(\frac{\pi}{2}\frac{\rho-\rho_b(\theta)}{\delta-\rho_b(\theta)}\right), \quad \theta < 0, \rho \geq \rho_b(\theta);$$

$$\cos^2\left(\frac{\pi}{2}\frac{\rho-(-\delta)}{\rho_b(\theta)-(-\delta)}\right), \quad \theta \geq 0, \rho < \rho_b(\theta);$$

$$0, \quad \theta \geq 0, \rho \geq \rho_b(\theta).$$

Figures 9A, 9B:
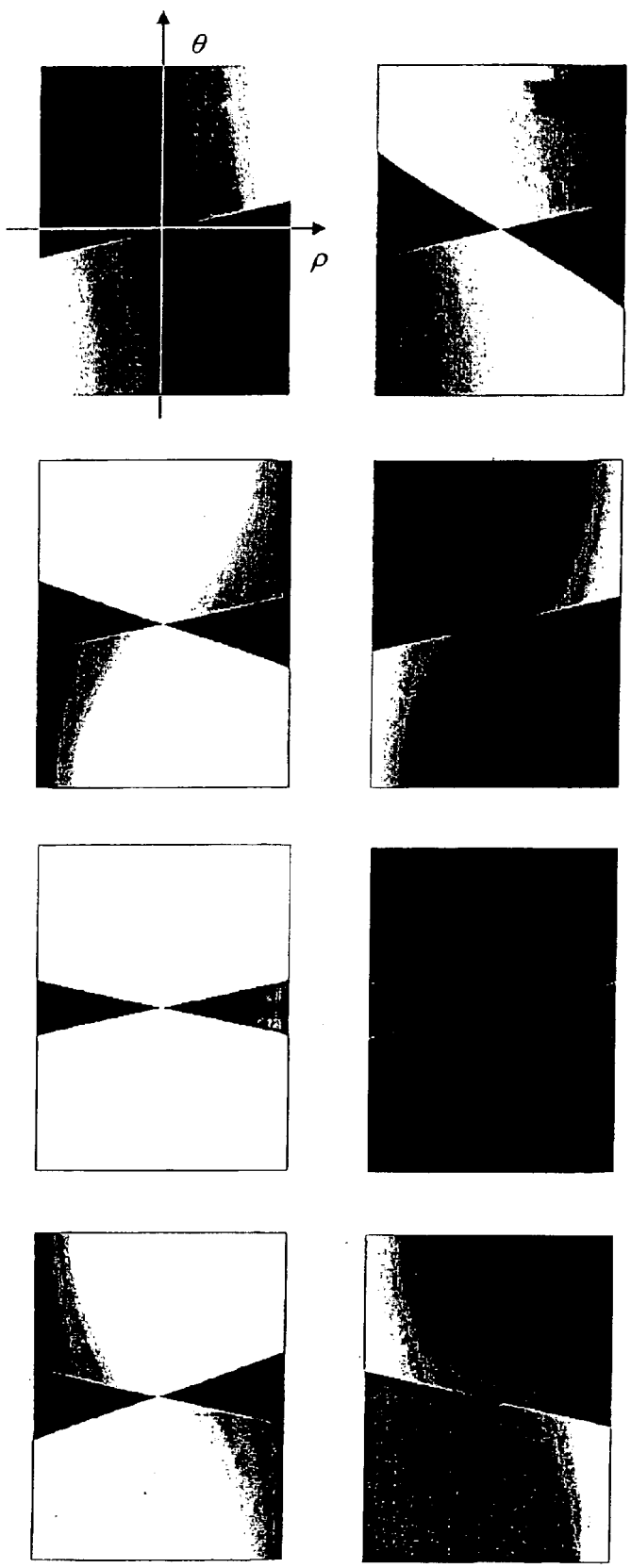
FIGS. 9($a$) and 9($b$) illustrate exemplary smooth weighting functions for the four maps shown in FIGS. 8($a$)–8($d$)

In the above weighting functions, $\delta$ is assumed to be the half size of the $\rho$ support and $\rho \in [-\delta,\delta]$. Some representative weighting functions are shown in FIGS. 9(a)–(b).

Interpolation/Extrapolation

Figure 10A:
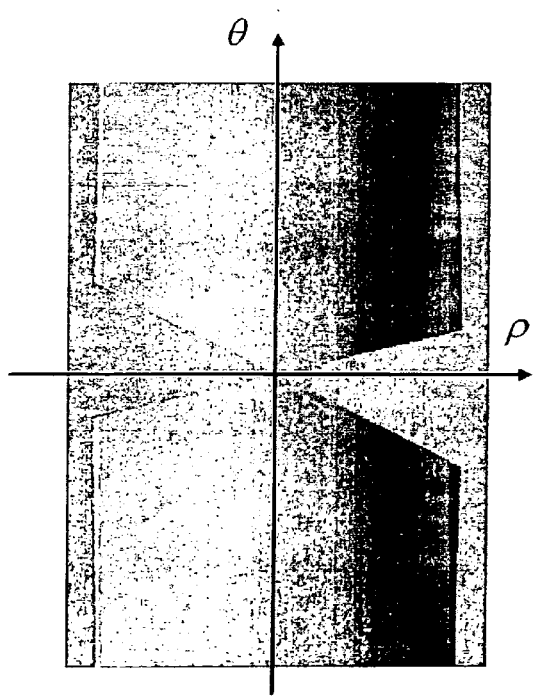
FIGS. 10($a$) and 10($b$) illustrate an exemplary first derivative Radon data of the 3D Shepp-Logan phantom after data filling with zero padding and linear interpolation, respectively.
Figure 10B:
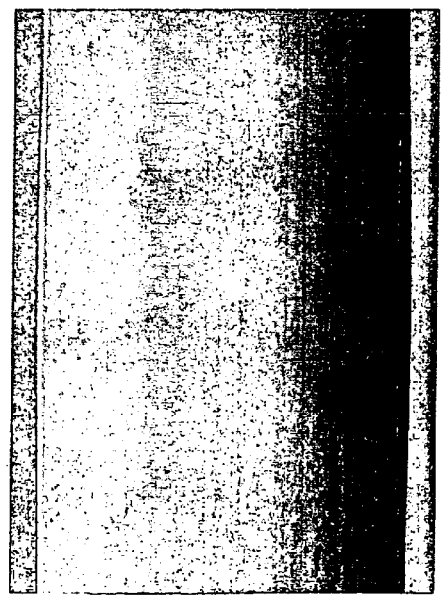

According to exemplary embodiments, zero-padding and linear interpolation methods may be used, respectively, to estimate missing data in the shadow zone. Grangeat reconstruction after zero padding is theoretically equivalent to the Feldkamp-type reconstruction. A few of Radon values near the shadow zone boundary can be linearly interpolated along $\theta$ direction. The zero padding and linear interpolation are shown in FIGS. 10(a) and 10(b).

Of course, there are multiple possibilities for interpolation/extrapolation into the shadow zone. Knowledge based interpolation/extrapolation is also feasible in this half-scan Grangeat framework. In addition, parallel-beam approximation of cone-beam projection data can be applied in this rebinning framework as well.

Exemplary Implementation of the Grangeat-Type Half-Scan Algorithm for the Circular Scanning Case To summarize, the Grangeat-type half-scan algorithm can, according to a first embodiment, be implemented in the following steps:

(1) Specify a characteristic point $(\rho,\theta,\phi)$ where the derivative of Radon data can be calculated;

(2) Determine the line integration points for the given characteristic point according to Eqs. (7), (8), and appropriate rebinning equations;

(3) Calculate the derivatives of Radon data;

(4) Calculate the smooth weighting functions $\omega_1(\rho,\theta,\phi)$ and $\omega_2(\rho,\theta,\phi)$;

(5) Apply the weighting functions to the Radon data;

(6) Repeat Steps 1–5 until we are done with all the characteristic points that can be calculated;

(7) Estimate the Radon data in the shadow zone; and (8) Reconstruct an image according to a Radon inversion formula.

Exemplary Simulation Results

Using a software simulator in the IDL Language (Research Systems Inc., Boulder, Colo.) for Grangeat-type image reconstruction, the numerical differentiation was performed with a built-in function based on 3-point Lagrangian interpolation. The source-to-origin distance was set to 3.92. The number of detectors per cone-beam projection was 256 by 256. The size of the 2D detector plane was 2.1 by 2.1. A half of the full-cone angle is about 15 degree. The number of projections was 210. The number of meridian planes was 180. The numbers of radial and angular samples were 256 and 360, respectively. Each reconstructed image volume had dimensions of 2.1 by 2.1 by 2.1, and contained 256 by 256 by 256 voxels. The numbers of samples were chosen to be greater than the lower bounds we established using the Fourier analysis method. Both the spherical phantom and the 3D Shepp-Logan phantom as shown in Table 1 were used in the numerical simulation.

TABLE 1

Parameters of the phantoms used in our numerical simulation.

| Phantom | a | b | C | x | y | z | θ | φ | Density |
|---|---|---|---|---|---|---|---|---|---|
| Sphere | 0.9 | 0.9 | 0.9 | 0.0 | 0.0 | 0.0 | 0.0 | 0.0 | 2.0 |
| Shepp-Logan | 0.69 | 0.9 | 0.92 | 0.0 | 0.0 | 0.0 | 0.0 | 0.0 | 2.0 |
| | 0.6624 | 0.88 | 0.874 | 0.0 | 0.0 | −0.0184 | 0.0 | 0.0 | −0.98 |
| | 0.41 | 0.21 | 0.16 | −0.22 | −0.25 | 0.0 | 0.0 | 72.0 | −0.02 |
| | 0.31 | 0.22 | 0.11 | 0.22 | −0.25 | 0.0 | 0.0 | −72.0 | −0.02 |
| | 0.21 | 0.35 | 0.25 | 0.0 | −0.25 | 0.35 | 0.0 | 0.0 | 0.01 |
| | 0.046 | 0.046 | 0.046 | 0.0 | −0.25 | 0.1 | 0.0 | 0.0 | 0.01 |
| | 0.046 | 0.02 | 0.023 | −0.08 | −0.25 | −0.605 | 0.0 | 0.0 | 0.01 |
| | 0.046 | 0.02 | 0.023 | 0.06 | −0.25 | −0.605 | 0.0 | 90.0 | 0.01 |
| | 0.056 | 0.1 | 0.04 | 0.06 | 0.625 | −0.105 | 0.0 | 0.0 | 0.01 |
| | 0.056 | 0.1 | 0.056 | 0.0 | 0.0625 | 0.1 | 0.0 | 0.0 | −0.02 |
| | 0.046 | 0.046 | 0.046 | 0.0 | −0.25 | −0.1 | 0.0 | 0.0 | 0.01 |
| | 0.023 | 0.023 | 0.023 | 0.0 | −0.25 | −0.605 | 0.0 | 0.0 | 0.01 |

Figure 11A:
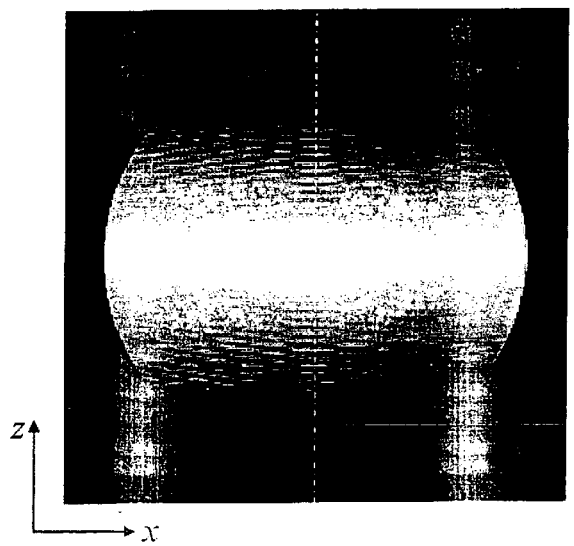
FIGS. 11($a$) and 11($b$) illustrate exemplary Grangeat-type half-scan reconstruction of the sphere phantom in the plane y=0 with zero-padding and linear interpolation, respectively.
Figure 11B:
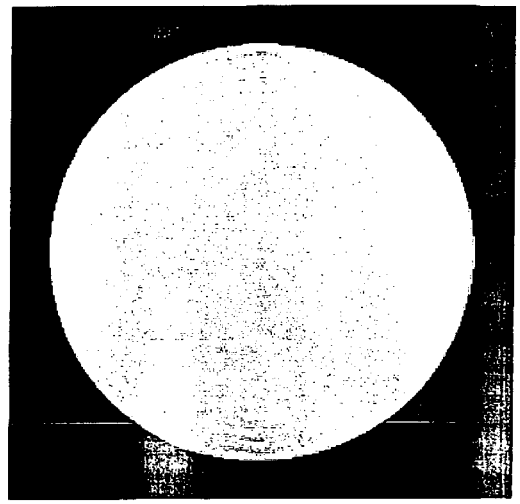
Figure 11C:
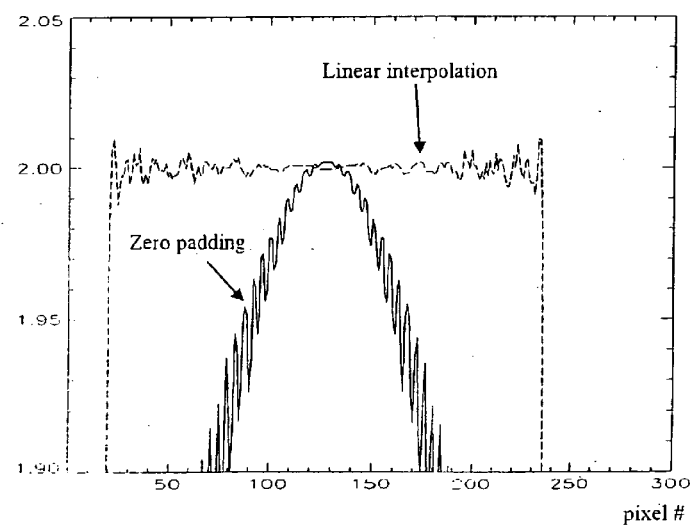

FIG. 11 shows the results obtained from the y=0 plane of the sphere phantom. The half-scan algorithm cannot produce exact reconstruction for a general object due to the incompleteness of projection data but in special cases like a sphere phantom this algorithm can achieve exact reconstruction with linear interpolation. When data in the shadow zone are linearly interpolated from the half-scan data of a sphere, exact reconstruction of the sphere can be achieved because the radon transform of a perfect sphere is linear. This exactness seems impossible with other half-scan cone-beam reconstruction algorithms. Nevertheless, this property is desirable in a number of major applications, such as micro-CT studies of spherical specimens.

Figures 12A, 12B:
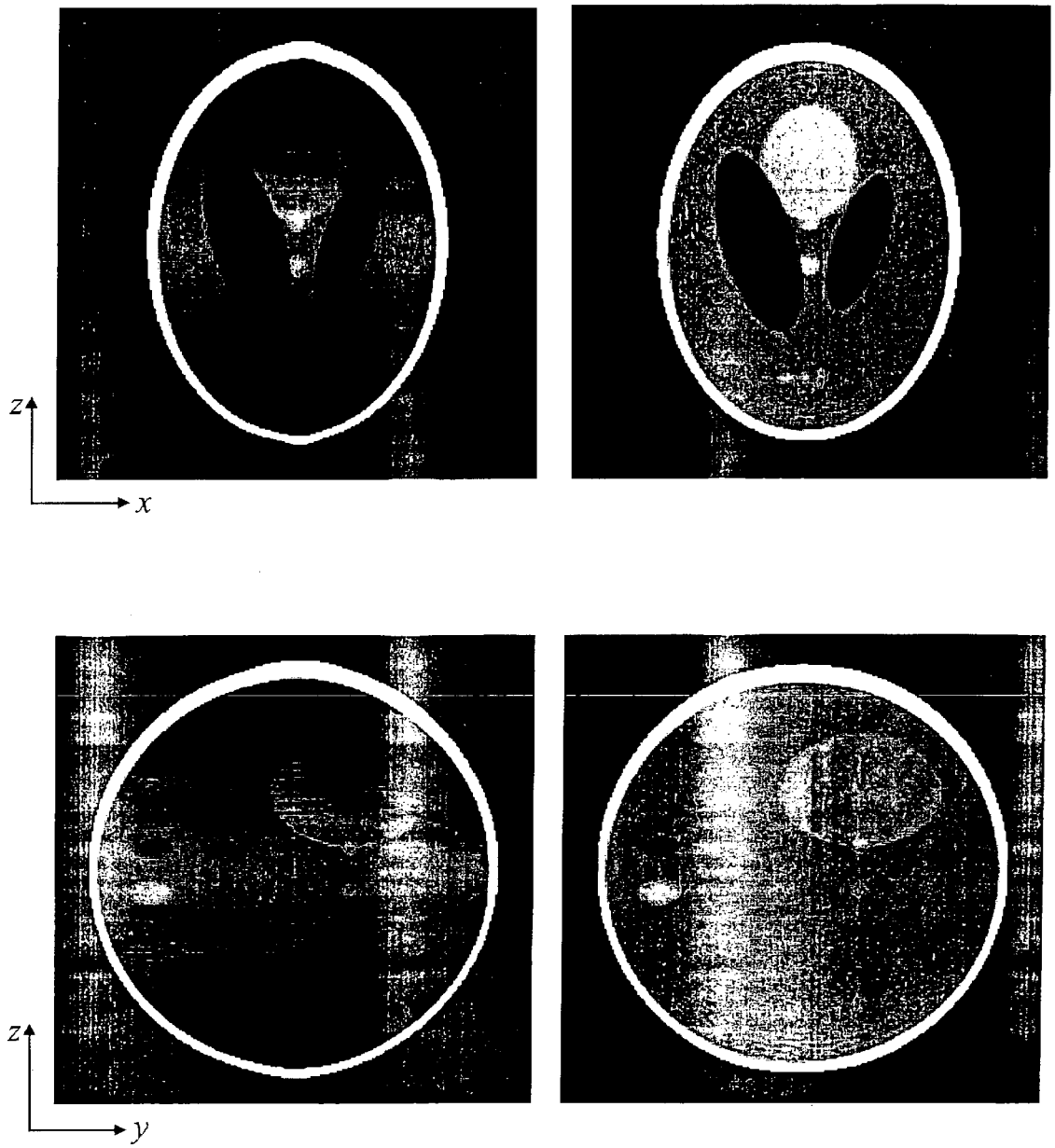
FIGS. 12($a$) and 12($b$) illustrate exemplary Grangeat-type half-scan reconstruction of the 3D Shepp-Logan phantom with zero-padding and linear interpolation, respectively.

FIG. 12 presents the results obtained from the y=0.242 and x=−0.0369 planes of the 3D Shepp-Logan phantom. With the zero-padding method, the low intensity drop away from the center plane was found to be more serious than that with the Feldkamp half-scan reconstruction. With the linear interpolation method, this type of artifacts was substantially eliminated.

Figure 13A:
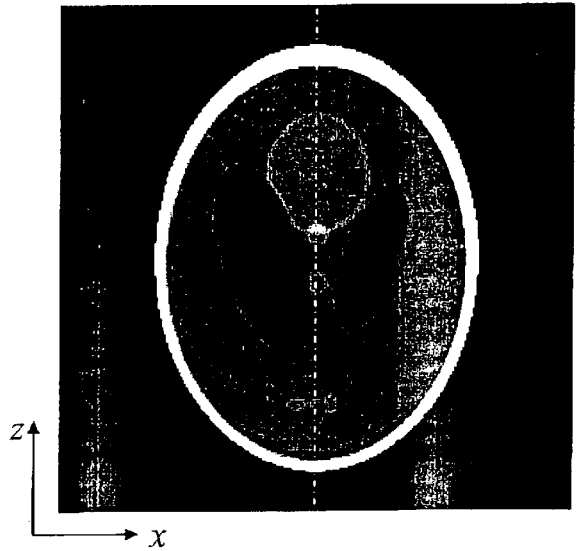
FIGS. 13($a$) and 13($b$) illustrate exemplary Grangeat-type reconstruction of the 3D Shepp-Logan phantom with full-scan reconstruction and half-scan reconstruction, respectively.
Figure 13B:
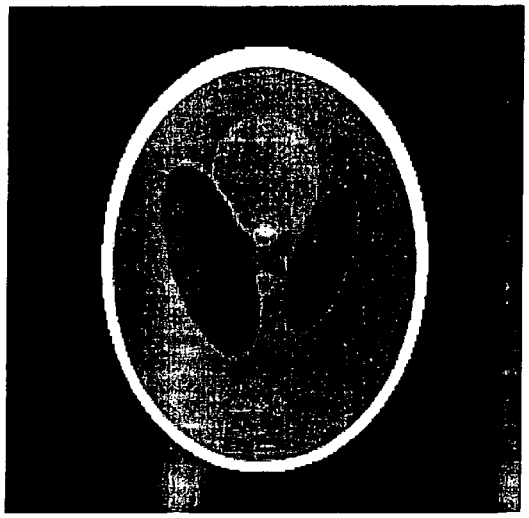
Figure 13C:
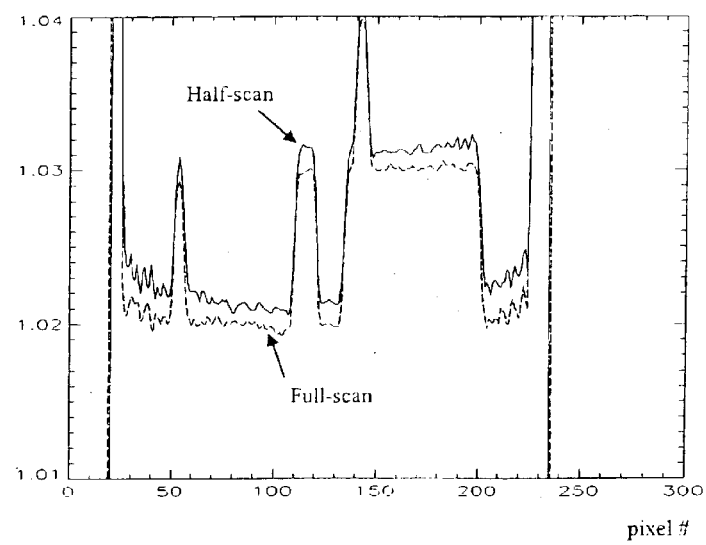

FIG. 13 compares the full-scan and half-scan Grangeat algorithms. Linear interpolation was applied with both algorithms. As compared to the Grangeat reconstruction in the full-scan case, little image degradation was visually perceived in all the Grangeat-type half-scan reconstructions performed.

Figures 14A, 14B, 14C:
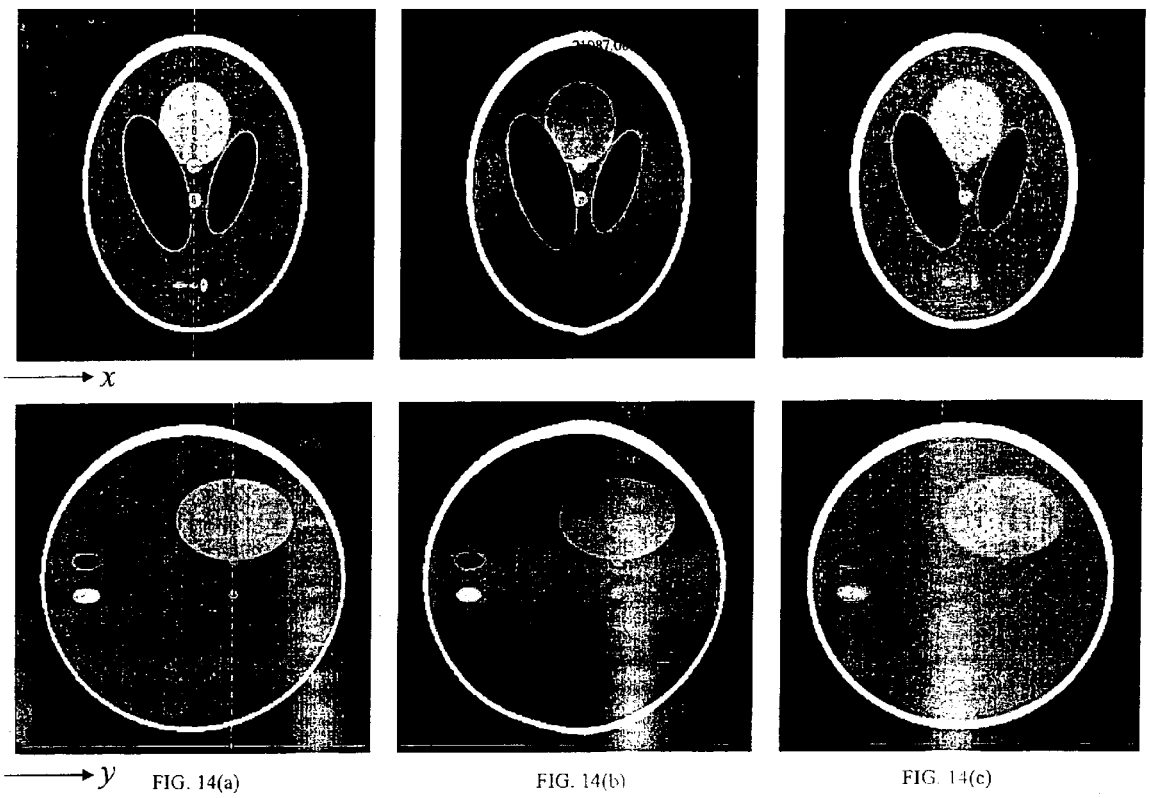
FIGS. 14($a$)–($c$) illustrate exemplary Feldkamp-type half-scan and Grangeat-type half-scan reconstructions with the original phantom, Feldkamp-type half-scan reconstruction, and Grangeat-type half-scan reconstruction, respectively.
Figure 14D:
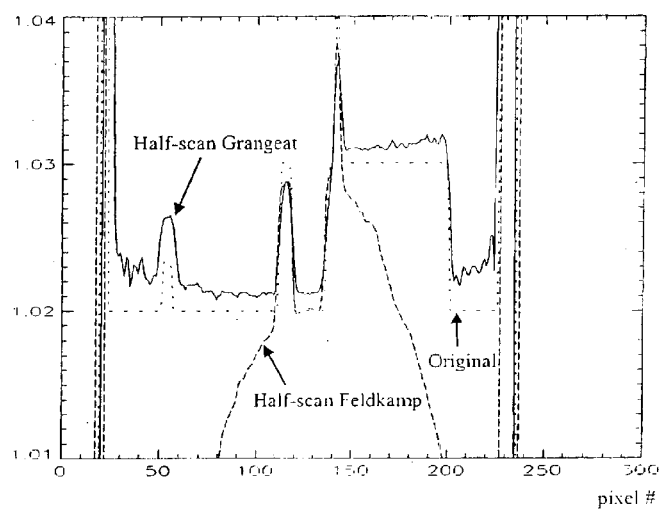

FIG. 14 compares Feldkamp-type half-scan reconstruction and Grangeat-type half-scan reconstruction.

In the first exemplary embodiment described above, a Grangeat-type half-scan algorithm is used in the circular scanning case. The half-scan spans 180 degrees plus two cone angles, allowing exact in-plane reconstruction. The smooth half-scan weighting functions have been designed for suppression of data inconsistence. Numerical simulation results have suggested the correctness and demonstrated the merits of our formulas. This Grangeat-type half-scan algorithm is considered promising for quantitative and dynamic biomedical applications of CT and micro-CT.

Grangeat-Type Helical Half-Scan CT Algorithm for Reconstruction of a Short Object According to a second embodiment, image reconstruction may be performed in the helical case without data truncation. In this embodiment, Grangeat's formula may be modified for utilization and estimation of Radon data. Specifically, each characteristic point may be characterized in the Radon space into singly, doubly, triply sampled, and shadow regions, respectively. A smooth weighting strategy is designed to compensate for data for redundancy and inconsistency. In the helical half-scan case, the concepts of projected trajectories and transition points on meridian planes are introduced to guide the design of weighting functions. Then, the shadow region is recovered via linear interpolation after smooth weighting. The Shepp-Logan phantom and other phantoms can be used to verify the correctness of the formulation, and demonstrate the merits of the Grangeat-type half-scan algorithm. The Grangeat-type helical half-scan algorithm is not only valuable for quantitative and/or dynamic biomedical applications of CT and micro-CT, but also serves as a basis in solving the long object problem.

Rebinning Equations for a Helical Trajectory

Figure 15:
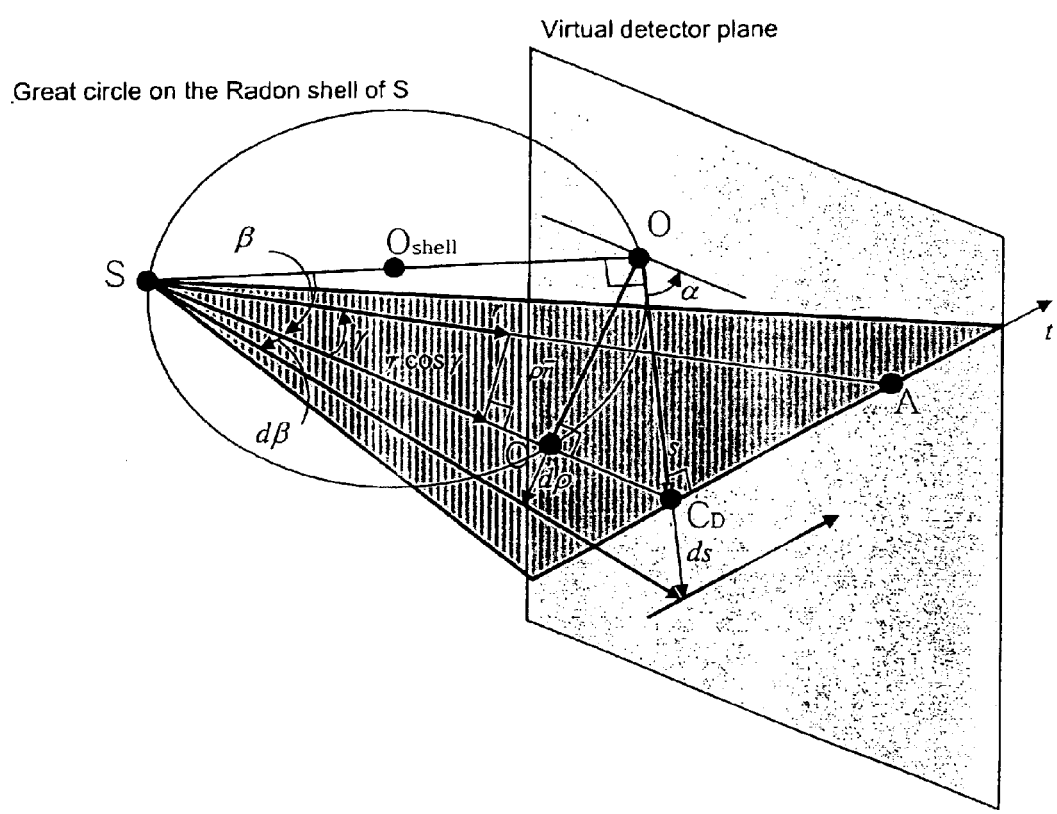
FIG. 15 depicts another illustration of exemplary Grangeat cone beam geometry according to exemplary embodiments.

The geometry for a helical half-scan is shown in FIG. 15, where (x,y,z) is the reference coordinate system, (y', z') denotes a meridian plane at $\phi$ from the x-axis, and the source vertex, $\lambda$, ranges from 0 to $\pi+2\gamma_m$. If the helical pitch is denoted by h, the source trajectory can be parameterized as $$\vec{a}(\lambda)=(SO \cos \lambda, SO \sin \lambda, h\lambda+z_0). \quad (24)$$

To compute the derivative of the Radon value at $\rho \vec{n}$, we need first calculate the line integration point $C_D$ on a detector plane, through which a line integration is performed along the line normal to $OC_D$. There is a geometrical relationship between the characteristic point $(\rho,\theta,\phi)$ and the line integration point $(s,\alpha,\lambda)$. In other words, we can find $(s,\alpha,\lambda)$ from $(\rho,\theta,\phi)$.

The 3D Radon value at a characteristic point $(\rho,\theta,\phi)$ is the integration of an object on a plane satisfying the following equation:

$$\vec{n} \cdot \vec{x} = \rho. \quad (25)$$

The intersection of the plane with the source trajectory is found by replacing $\vec{x}$ with $\vec{a}(\lambda)$ to solve $$\vec{n} \cdot \vec{a}(\lambda) = \rho \quad (26)$$

where $\vec{n}=(\sin \theta \cos \phi, \sin \theta \sin \phi, \cos \theta)$ denotes a unit vector towards the corresponding characteristic point, and $\vec{a}(\lambda)=(R \cos \lambda, R \sin \lambda, h\lambda+z_0)$ the source position. The equation can be written as:

$$\begin{cases} R\cos\lambda\sin\theta\cos\varphi + R\sin\lambda\sin\theta\sin\varphi + (h\lambda + z_0)\cos\theta - \rho = 0 \\ R\sin\theta(\cos\lambda\cos\varphi + \sin\lambda\sin\varphi) + (h\lambda + z_0)\cos\theta = \rho \end{cases} \quad (27)$$

While we can calculate the line integration point analytically in a circular trajectory case, we can only do it numerically in a helical trajectory case. Once we acquire $\lambda$, we have line integration point $(\alpha,s)$ on the detector plane $D_\psi$, where $$\psi = \lambda + \frac{\pi}{2}.$$

The equations are expressed as:

$$\alpha = \tan^{-1}\left(\frac{\cot\theta}{\sin(\varphi - \lambda)}\right) \quad (28)$$

$$s = \frac{(\rho - (h\lambda + z_0)\cos\theta)\sin\alpha}{\cos\theta}. \quad (29)$$

Therefore, the Radon value at the characteristic point defined by $(\rho,\theta,\phi)$ can be calculated by the integration along the line represented by $(s,\alpha,\lambda)$ according to Eqs. 27–29.

Grangeat-Type Helical Half-Scan Formula

With a circular half-scan, there are three types of regions: shadow, singly and doubly sampled regions, respectively. With a helical half-scan, in addition to those three types of regions, there may be triply sampled regions as well. They are schematically illustrated in FIGS. 18(a)–(d). Hence, the Grangeat-type helical half-scan formula must be in the following format:

$$\frac{\partial}{\partial \rho} Rf(\rho\vec{n}) = \sum_{g=1}^{3} \omega_g R'_g f(\rho\vec{n}), \quad (30)$$

where $\omega_g$ denote the weighting functions, g is a group identifier to be explained in detail later, and $$R'_g f(\rho\vec{n}) = \frac{1}{\cos^2\beta} \frac{\partial}{\partial s} \int_{-\infty}^{\infty} \frac{SO}{SA} Xf(s, t, \lambda) dt. \quad (31)$$

The form is basically the same as that with a circular half-scan trajectory but three weighting functions and corresponding Radon values are needed for each characteristic point, while we only need two weighting functions in a circular half-scan case.

In Eq. (31), the value of the group identifier g is determined according to the following criteria:

$$g = 1, \quad 0 \leq \lambda \leq \lambda_{t1}, \quad (32)$$
$$\quad 2, \quad \lambda_{t1} < \lambda \leq \lambda_{t2},$$
$$\quad 3, \quad \lambda_{t2} < \lambda \leq \pi + 2\gamma_m.$$

where $\lambda_{t1}$ and $\lambda_{t2}$ are tangential vertices and will be explained in detail below. This means that the calculated Radon data must belong to one of the three groups depending on the $\lambda$. Regarding the weighting functions, they must satisfy $$\sum_{g=1}^{3} \omega_g = 1 \tag{33}$$

If we assume that there is no motion or data inconsistency during the scan, we can simply average Radon data from different vertices. In this case, the weighting functions become discontinuous. However, in real situations, motion effects and data inconsistency should be taken into account. Then, the discontinuous weighting functions could cause artifacts. Therefore, the smooth weighting functions are needed for satisfactory image quality, as explained below.

Weighting Functions

The concepts of projected trajectory and transition points are needed before our weighting functions are designed.

Projected Trajectory on a Meridian Plane at $\phi$

Figure 17:
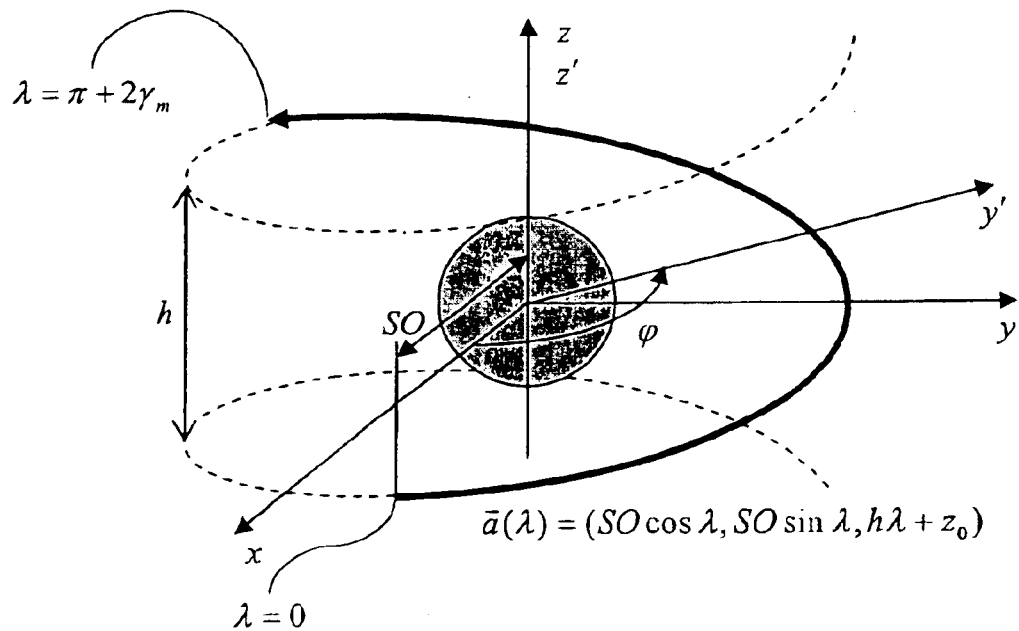
FIG. 17 illustrates exemplary helical half-scan geometry as it relates to the second embodiment.
Figure 18A:
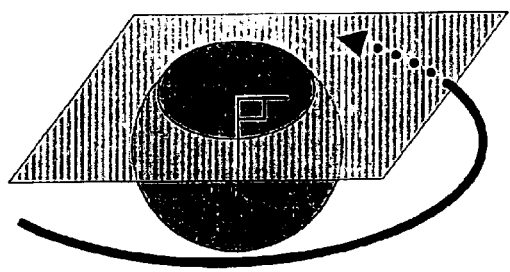
FIGS. 18($a$)–($d$) illustrate exemplary classification of the Radon space in the shadow region, singly sampled region, doubly sampled region, and triply sampled region, respectively.
Figure 18B:
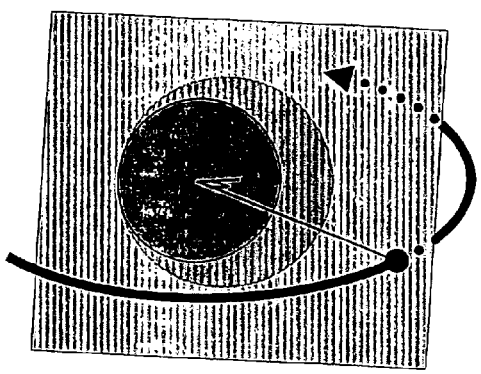
Figure 18C:
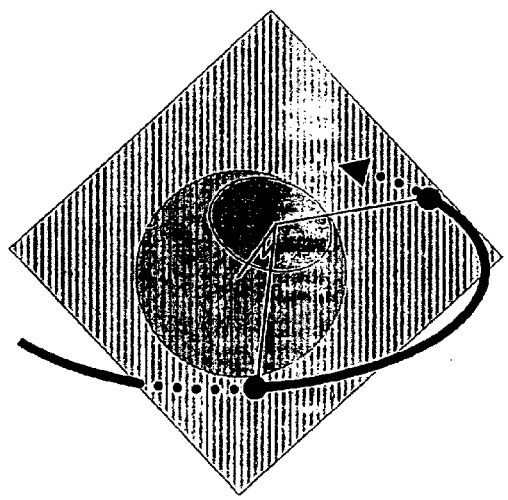
Figure 18D:
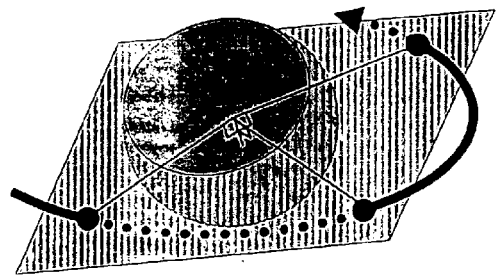
Figure 19A:
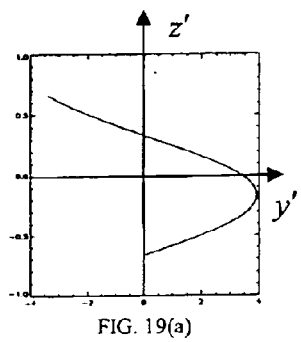
FIGS. 19(a)–19(i) illustrate exemplary projected trajectories on meridian planes of φ=90°, 110°, 130°, 150°, 170°, 190°, 210°, 230°, and 250° respectively.
Figure 19B:
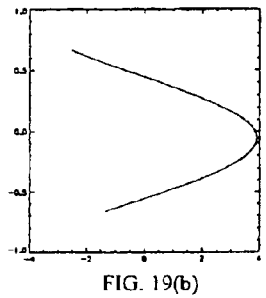
Figure 19C:
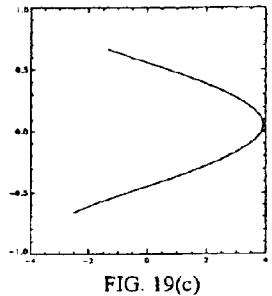
Figure 19D:
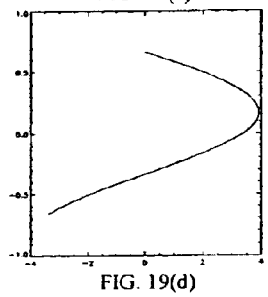
Figure 19E:
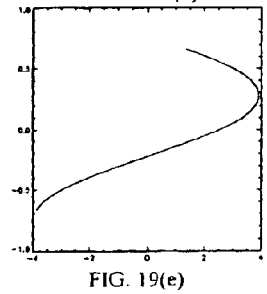
Figure 19F:
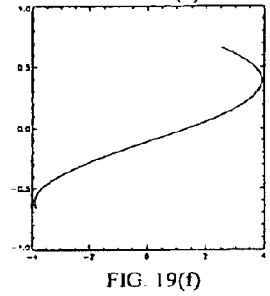
Figure 19G:
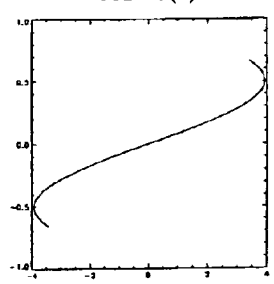
Figure 19H:
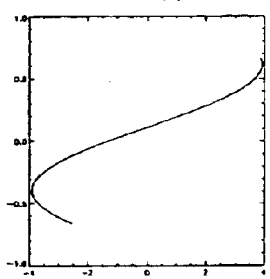
Figure 19I:
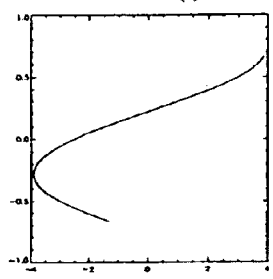
Figures 21A, 21B, 21C, 21D:
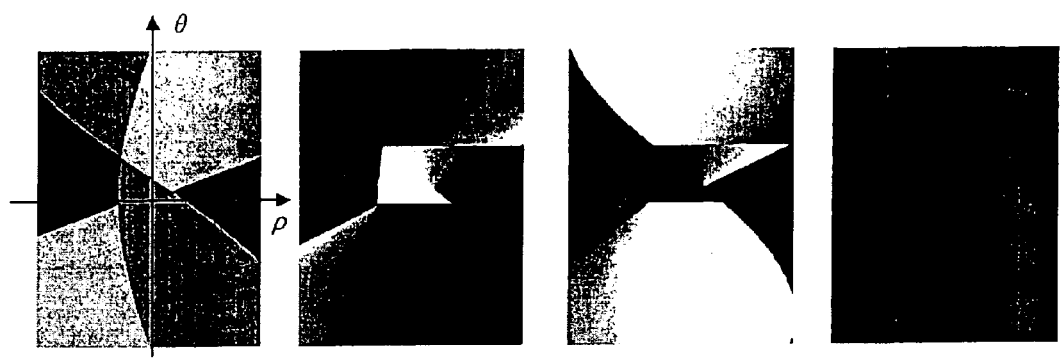
FIGS. 21(a)–(d), FIGS. 21(e)–(h), and FIGS. 21(i)–(l) illustrate exemplary region map and weighting functions for meridian planes at φ=90°, φ=170°, and φ=250°, respectively.
Figures 21E, 21F, 21G, 21H:
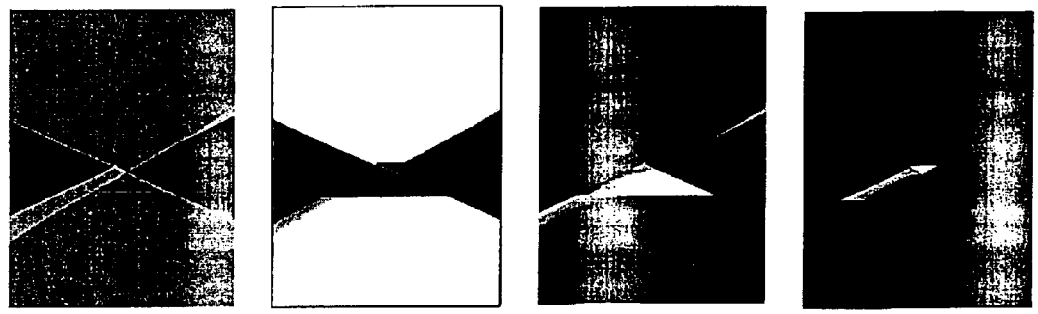
Figures 21I, 21J, 21K, 21L:
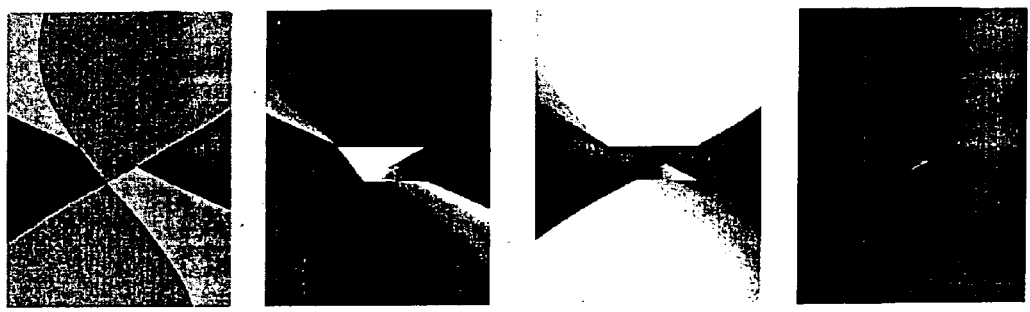

The projected trajectory on a meridian plane at $\phi$ is useful for design of the weighting functions. Several projected trajectories on different meridian planes are shown in FIGS. 19(a)–19(i). The source trajectory of Eq. (24) is first transformed from (x,y,z) to (x',y',z') coordinate systems, as shown in FIG. 17. Therefore, for a given meridian plane at $\phi$, the projected trajectory on this plane is described as $$\begin{cases} y' = SO\sin(\lambda - (\varphi - \frac{\pi}{2})), \\ z' = h\lambda + z_0 \end{cases} \tag{34}$$

Dashed lines in FIG. 20(a) represent the planes normal to the meridian plane. The integration result(s) on the plane(s) corresponding to each line must be equal to the Radon value at $(\rho,\theta,\phi)$. In the Grangeat framework, the derivative of Radon data is calculated from the detector planes as denoted by the colored lines associated with the intersected vertex points. Geometrically, there can be maximally three intersection points. For a given $(\theta,\phi)$, the number of intersecting points determines the degree of redundancy and depends on $\rho$.

Transition Points on the Projected Trajectory

Every projected trajectory has two end points expressed by $$\vec{e}_1 = (y', z') = (SO\sin(0 - (\varphi - \frac{\pi}{2})), 0 + z_0), \tag{35}$$

$$\vec{e}_1 = (y', z') = (SO\sin((\pi + 2\gamma_m) - (\varphi - \frac{\pi}{2})), h(\pi + 2\gamma_m) + z_0). \tag{36}$$

For a given $\theta$ on a meridian plane $\phi$, there may be planes normal to $\vec{\theta}$ and tangent to the projected trajectory. The tangential points can be analytically specified by $$\vec{t}_1 = (y, z) = (SO\sin(\lambda_{t1} - (\varphi - \frac{\pi}{2})), h\lambda_{t1} + z_0), \tag{37}$$

$$\vec{t}_2 = (y, z) = (SO\sin(\lambda_{t2} - (\varphi - \frac{\pi}{2})), h\lambda_{t2} + z_0), \tag{38}$$

where $\lambda_{t1}$, $\lambda_{t2}$ are calculated in the following.

A projected trajectory on a meridian plane is determined as $$y = SO\sin(\lambda - (\varphi - \frac{\pi}{2})), \tag{39}$$

$$z = h\lambda + z_0. \tag{40}$$

To express $\lambda$ as a function of z, we obtain $$\lambda = \frac{z - z_0}{h}, \tag{41}$$

substitute Eq. (43) into Eq. (41), and have $$y = SO\sin\left(\frac{z - z_0}{h} - (\varphi - \frac{\pi}{2})\right). \tag{42}$$

Then, we compute the derivative and set it to the slope of the colored line:

$$\frac{dy}{dz} = \frac{1}{h}SO\cos\left(\frac{z - z_0}{h} - (\varphi - \frac{\pi}{2})\right) = -\cot\theta. \tag{43}$$

In other words, $$z = h\left(\cos^{-1}\left(-\frac{h}{SO}\cot\theta\right) + (\varphi - \frac{\pi}{2})\right) + z_0. \tag{44}$$

Then, we have $$\lambda = \left(\cos^{-1}\left(-\frac{h}{SO}\cot\theta\right) + (\varphi - \frac{\pi}{2})\right). \tag{45}$$

The solution of this equation is meaningful only when $0 \leq \lambda \leq \pi + 2\gamma_m$, resulting in up to two solutions: $\lambda_{t1}$ and $\lambda_{t2}$. It is assumed that $\lambda_{t2}$ is greater than $\lambda_{t1}$ if it exists. Recall that these $\lambda_{t1}$ and $\lambda_{t2}$ are used for grouping vertices as described above.

In terms of the above end points and tangential points, we can find the transition points $\rho$ as follows:

$$\rho_{e1} = \vec{\theta} \cdot \vec{e}_1$$

$$\rho_{e2} = \vec{\theta} \cdot \vec{e}_2$$

$$\rho_{t1} = \vec{\theta} \cdot \vec{t}_1$$

$$\rho_{t2} = \vec{\theta} \cdot \vec{t}_2, \tag{46}$$

where $\vec{\theta} = (y,z) = (\sin\theta, \cos\theta)$. As shown in FIG. 20(a) the type of a region can be identified according to the following criterion: $\rho_{t2} \leq \rho \leq \rho_{e2}$, indicating a doubly sampled region; $\rho_{e2} < \rho < \rho_{e1}$, a singly sampled region; $\rho_{e1} \leq \rho \leq \rho_{t1}$, a doubly sampled region.

Smooth Weighting Functions

Weighting functions are designed in reference to $\rho_{e1}$, $\rho_{e2}$, $\rho_{t1}$, $\rho_{t2}$, which are functions of $\theta$ and $\phi$. Mathematically speaking, there are up to two possibilities when we have neither $\rho_{t1}$ nor $\rho_{t2}$, which are $\rho_{e1} \geq \rho_{e2}$ and $\rho_{e1} \leq \rho_{e2}$. Similarly, there are up to six cases when we have only either $\rho_{t1}$ or $\rho_{t2}$. Furthermore, there are up to twenty-four cases when we have both $\rho_{t1}$ and $\rho_{t2}$. However, all the statements are not meaningful after our case-by-case inspection. It is found that there exist only eleven cases actually. For example, in absence of $\rho_{t1}$ and $\rho_{t2}$, we always have the case of $\rho_{e1} \leq \rho_{e2}$, and never have the case of $\rho_{e1} \geq \rho_{e2}$. Similarly, it is impossible to have the cases of $\rho_{e1} \leq \rho_{t1} \leq \rho_{e2}$ and $\rho_{e2} \leq \rho_{t1} \leq \rho_{e1}$ in absence of $\rho_{t2}$. Those eleven cases are: i) $\rho_{e1} \leq \rho_{e2}$ in absence of $\rho_{t1}$ and $\rho_{t2}$; ii) $\rho_{t1} \leq \rho_{e1} \leq \rho_{e2}$ in absence $\rho_{t2}$; iii) $\rho_{e2} \leq \rho_{e1} \leq \rho_{t1}$ in absence of $\rho_{t2}$; iv) $\rho_{t1} \leq \rho_{e2} \leq \rho_{e1}$ in absence of $\rho_{t2}$; v) $\rho_{e1} \leq \rho_{e2} \leq \rho_{t1}$ in absence of $\rho_{t2}$; vi) $\rho_{t2} \leq \rho_{e2} \leq \rho_{e1} \leq \rho_{t1}$; vii) $\rho_{t1} \leq \rho_{e1} \leq \rho_{e2} \leq \rho_{t2}$; viii) $\rho_{e1} \leq \rho_{t2} \leq \rho_{t1} \leq \rho_{e2}$; ix) $\rho_{t2} \leq \rho_{e1} \leq \rho_{e2} \leq \rho_{t1}$; x) $\rho_{t2} \leq \rho_{e1} \leq \rho_{t1} \leq \rho_{e2}$; xi) $\rho_{e1} \leq \rho_{t2} \leq \rho_{e2} \leq \rho_{t1}$.

In addition to our geometric analysis on projected trajectories on the meridian plane, we did exclusive numerical simulation to confirm that there are only the above eleven meaningful cases. For all the $(\theta,\phi)$, we calculated the transition points, sorted the $\rho$ values, and decided which one of the mathematically possible thirty two cases it belongs to. Once a specific case was found, we set the flag for that case on. After this kind of numerical verification, we eliminated the cases that never happened. Also, we repeated the simulation with respect to representative combinations of imaging parameters, including the source-to-origin distance, helical pitch and cone angle $(2\gamma_m)$. Finally, it was confirmed that there are indeed only the above eleven cases that are feasible.

For each of those meaningful cases, smooth weighing functions are designed in terms of $\rho_{e1}, \rho_{e2}, \rho_{t1}, \rho_{t2}$. The two general requirements are that (1) the sum of the weighs for each characteristic point be one, and (2) the weight profile along the $\rho$ direction be continuous. To further understand the designing processing, some representative illustrations are considered helpful. FIG. 20(b) represents the case where there is neither $\rho_{t1}$ nor $\rho_{t2}$ for given $(\theta,\phi)$, and only group 1 exists. Therefore, $\omega_1=1$, and $\omega_2$ and $\omega_3$ are set to zero. FIG. 20(c) corresponds to the case where there is one tangential point, and two groups are available. The trajectory from $\vec{e}_1$ to $\vec{t}_1$ belongs to group 1, while that from $\vec{t}_1$ to $\vec{e}_2$ belongs to group 2. The weighting function for group 1, $\omega_1$, is designed to change gradually from 1 to 0 along the projected trajectory from $\rho_{t1}$ to $\rho_{e1}$, while the weighting function for group 2, $\omega_2$, increases from 0 to 1 in the same interval, and stays constant between $\rho_{e1}$ and $\rho_{e2}$. $\omega_3$ is set to zero since there is no group 3. Of course, the sum of the weighting functions should be made one. FIG. 20(d) illustrates the case where there are two tangential points, and we have group 1 between $\vec{e}_1$ and $\vec{t}_1$, group 2 between $\vec{t}_1$ and $\vec{t}_2$, and group 3 between $\vec{t}_e$ and $\vec{e}_2$. The weighting function for the group 1, $\omega_1$, should be one between $\rho_{e1}$ to $\rho_{t2}$, and smoothly change from 1 to 0 along the projected trajectory from $\rho_{t1}$ to $\rho_{e1}$. The weighting function for the group 3, $\omega_3$, should smoothly change from 0 to 1 along the trajectory from $\rho_{t2}$ to $\rho_{t1}$, and be 0 between $\rho_{t1}$ and $\rho_{e2}$. The weighting function for the group 2, $\omega_2$, is designed to smoothly increase from 0 at $\rho_{t2}$ until it reaches the middle point between $\rho_{t2}$ and $\rho_{t1}$, and decrease to 0 at $\rho_{t1}$.

Some representative distributions of the weighting functions are included in FIGS. 21(a)–(l). The weighting functions are formulated as follows, keyed to each of the feasible cases:

i) $\rho_{e1} \leq \rho_{e2}$ in absence of $\rho_{t1}$ and $\rho_{t2}$:
$\omega_1 = 1$,
$\omega_2 = 0$,
$\omega_3 = 0$.

ii) $\rho_{t1} \leq \rho_{e1} \leq \rho_{e2}$ in absence $\rho_{t2}$:

$$\omega_1 = \cos^2\left(\frac{\pi}{2}\frac{\rho - \rho_{t1}}{\rho_{e1} - \rho_{t1}}\right), \quad \rho_{t1} \leq \rho \leq \rho_{e1}$$
$$0, \quad \rho_{e1} < \rho \leq \rho_{e2}$$

$$\omega_2 = \sin^2\left(\frac{\pi}{2}\frac{\rho - \rho_{t1}}{\rho_{e1} - \rho_{t1}}\right), \quad \rho_{t1} \leq \rho \leq \rho_{e1}$$
$$1, \quad \rho_{e1} < \rho \leq \rho_{e2}$$

$\omega_3 = 0$ iii) $\rho_{e2} \leq \rho_{e1} \leq \rho_{t1}$ in absence of $\rho_{t2}$:

$$\omega_1 = 0, \quad \rho_{e2} \leq \rho < \rho_{e1}$$
$$\sin^2\left(\frac{\pi}{2}\frac{\rho - \rho_{e1}}{\rho_{t1} - \rho_{e1}}\right), \quad \rho_{e1} \leq \rho \leq \rho_{t1}$$
$$\omega_2 = 1, \quad \rho_{e1} \leq \rho < \rho_{e2}$$
$$\cos^2\left(\frac{\pi}{2}\frac{\rho - \rho_{e1}}{\rho_{t1} - \rho_{e1}}\right), \quad \rho_{e2} \leq \rho \leq \rho_{t1}$$

$\omega_3 = 0$ iv) $\rho_{t1} \leq \rho_{e2} \leq \rho_{e1}$ in absence of $\rho_{t2}$:

$$\omega_1 = \sin^2\left(\frac{\pi}{2}\frac{\rho - \rho_{t1}}{\rho_{e2} - \rho_{t1}}\right), \quad \rho_{t1} \leq \rho \leq \rho_{e2}$$
$$1, \quad \rho_{e2} < \rho \leq \rho_{e1}$$

$$\omega_2 = \cos^2\left(\frac{\pi}{2}\frac{\rho - \rho_{t1}}{\rho_{e2} - \rho_{t1}}\right), \quad \rho_{t1} \leq \rho \leq \rho_{e2}$$
$$0, \quad \rho_{e2} < \rho \leq \rho_{e1}$$

$\omega_3 = 0$ v) $\rho_{e1} \leq \rho_{e2} \leq \rho_{t1}$ in absence of $\rho_{t2}$:

$$\omega_1 = 1, \quad \rho_{e1} \leq \rho < \rho_{e2}$$
$$\cos^2\left(\frac{\pi}{2}\frac{\rho - \rho_{e2}}{\rho_{t1} - \rho_{e2}}\right), \quad \rho_{e2} \leq \rho \leq \rho_{t1}$$
$$\omega_2 = 0, \quad \rho_{e1} \leq \rho < \rho_{e2}$$
$$\sin^2\left(\frac{\pi}{2}\frac{\rho - \rho_{e2}}{\rho_{t1} - \rho_{e2}}\right), \quad \rho_{e2} \leq \rho \leq \rho_{t1}$$

$\omega_3 = 0$ vi) $\rho_{t2} \leq \rho_{e2} \leq \rho_{e1} \leq \rho_{t1}$ $$\omega_1 = 0, \quad \rho_{t2} \leq \rho \leq \rho_{e2}$$
$$0, \quad \rho_{e2} < \rho < \rho_{e1}$$
$$\sin^2\left(\frac{\pi}{2}\frac{\rho - \rho_{e1}}{\rho_{t1} - \rho_{e1}}\right), \quad \rho_{e1} \leq \rho \leq \rho_{t1}$$
$$\omega_2 = \sin^2\left(\frac{\pi}{2}\frac{\rho - \rho_{t2}}{\rho_{e2} - \rho_{t2}}\right), \quad \rho_{t2} \leq \rho \leq \rho_{e2}$$
$$1, \quad \rho_{e2} < \rho < \rho_{e1}$$
$$\cos^2\left(\frac{\pi}{2}\frac{\rho - \rho_{e1}}{\rho_{t1} - \rho_{e1}}\right), \quad \rho_{e1} \leq \rho \leq \rho_{t1}$$

$$\omega_3 = \cos^2\left(\frac{\pi}{2}\frac{\rho - \rho_{t2}}{\rho_{e2} - \rho_{t2}}\right), \quad \rho_{t2} \leq \rho \leq \rho_{e2}$$
$$0, \quad \rho_{e2} < \rho < \rho_{e1}$$
$$0, \quad \rho_{e1} \leq \rho \leq \rho_{t1}$$

vii) $\rho_{t1} \leq \rho_{e1} \leq \rho_{e2} \leq \rho_{t2}$ $$\omega_1 = \cos^2\left(\frac{\pi}{2}\frac{\rho - \rho_{t1}}{\rho_{e1} - \rho_{t1}}\right), \quad \rho_{t1} \leq \rho \leq \rho_{e1}$$
$$0, \quad \rho_{e1} < \rho < \rho_{e2}$$
$$0, \quad \rho_{e2} \leq \rho \leq \rho_{t2}$$

$$\omega_2 = \sin^2\left(\frac{\pi}{2}\frac{\rho - \rho_{t1}}{\rho_{e1} - \rho_{t1}}\right), \quad \rho_{t1} \leq \rho \leq \rho_{e1}$$
$$1, \quad \rho_{e1} < \rho \leq \rho_{e2}$$
$$\cos^2\left(\frac{\pi}{2}\frac{\rho - \rho_{e2}}{\rho_{t2} - \rho_{e2}}\right), \quad \rho_{e2} \leq \rho \leq \rho_{t2}$$

$$\omega_3 = 0, \quad \rho_{t1} \leq \rho \leq \rho_{e1}$$
$$0, \quad \rho_{e1} < \rho < \rho_{e2}$$
$$\sin^2\left(\frac{\pi}{2}\frac{\rho - \rho_{e2}}{\rho_{t2} - \rho_{e2}}\right), \quad \rho_{e2} \leq \rho \leq \rho_{t2}$$

viii) $\rho_{e1} \leq \rho_{t2} \leq \rho_{t1} \leq \rho_{e2}$ $$\omega_1 = 1, \quad \rho_{e1} \leq \rho < \rho_{t2}$$
$$\cos^2\left(\pi\frac{\rho - \rho_{t2}}{\rho_{t1} - \rho_{t2}}\right), \quad \rho_{t2} \leq \rho < \rho_{t2} + (\rho_{t1} - \rho_{t2})/2$$
$$0, \quad \rho_{t2} + (\rho_{t1} - \rho_{t2})/2 \leq \rho \leq \rho_{t1}$$
$$0, \quad \rho_{t1} < \rho \leq \rho_{e2}$$

$$\omega_2 = 0, \quad \rho_{e1} \leq \rho < \rho_{t2}$$
$$\sin^2\left(\pi\frac{\rho - \rho_{t2}}{\rho_{t1} - \rho_{t2}}\right), \quad \rho_{t2} \leq \rho < \rho_{t2} + (\rho_{t1} - \rho_{t2})/2$$
$$\sin^2\left(\pi\frac{\rho - \rho_{t2}}{\rho_{t1} - \rho_{t2}}\right), \quad \rho_{t2} + (\rho_{t1} - \rho_{t2})/2 \leq \rho \leq \rho_{t1}$$
$$0, \quad \rho_{t1} < \rho \leq \rho_{e2}$$

$$\omega_3 = 0, \quad \rho_{e1} \leq \rho \leq \rho_{t2}$$
$$0, \quad \rho_{t2} \leq \rho < \rho_{t2} + (\rho_{t1} - \rho_{t2})/2$$
$$\cos^2\left(\pi\frac{\rho - \rho_{t2}}{\rho_{t1} - \rho_{t2}}\right), \quad \rho_{t2} + (\rho_{t1} - \rho_{t2})/2 \leq \rho \leq \rho_{t1}$$
$$1, \quad \rho_{t1} < \rho \leq \rho_{e2}$$

ix) $\rho_{t2} \leq \rho_{e1} \leq \rho_{e2} \leq \rho_{t1}$ $$\omega_1 = 0, \quad \rho_{t2} \leq \rho < \rho_{e1}$$
$$\frac{1}{2}\sin^2\left(\frac{\pi}{2}\frac{\rho - \rho_{e1}}{\rho_{e2} - \rho_{e1}}\right), \quad \rho_{e1} \leq \rho \leq \rho_{e2}$$
$$\frac{1}{2}, \quad \rho_{e2} < \rho \leq \rho_{t1}$$

$$\omega_2 = \frac{1}{2}, \quad \rho_{t2} \leq \rho < \rho_{e1}$$
$$\frac{1}{2}, \quad \rho_{e1} \leq \rho \leq \rho_{e2}$$
$$\frac{1}{2}, \quad \rho_{e2} < \rho \leq \rho_{t1}$$

$$\omega_3 = \frac{1}{2}, \quad \rho_{t2} \leq \rho < \rho_{e1}$$
$$\frac{1}{2}\cos^2\left(\frac{\pi}{2}\frac{\rho - \rho_{e1}}{\rho_{e2} - \rho_{e1}}\right), \quad \rho_{e1} \leq \rho \leq \rho_{e2}$$
$$0, \quad \rho_{e2} < \rho \leq \rho_{t1}$$

x) $\rho_{t2} \leq \rho_{e1} \leq \rho_{t1} \leq \rho_{e2}$ $$\omega_1 = 0, \quad \rho_{t2} \leq \rho < \rho_{e1}$$
$$\sin^2\left(\pi\frac{\rho - \rho_{e1}}{\rho_{t1} - \rho_{e1}}\right), \quad \rho_{e1} \leq \rho < \rho_{e1} + (\rho_{t1} - \rho_{e1})/2$$
$$\sin^2\left(\pi\frac{\rho - \rho_{e1}}{\rho_{t1} - \rho_{e1}}\right), \quad \rho_{e1} + (\rho_{t1} - \rho_{e1})/2 \leq \rho \leq \rho_{t1}$$
$$0, \quad \rho_{t1} < \rho \leq \rho_{e2}$$

$$\omega_2 = \frac{1}{2}, \quad \rho_{t2} \leq \rho < \rho_{e1}$$
$$\frac{1}{2}\cos^2\left(\pi\frac{\rho - \rho_{e1}}{\rho_{t1} - \rho_{e1}}\right), \quad \rho_{e1} \leq \rho < \rho_{e1} + (\rho_{t1} - \rho_{e1})/2$$
$$0, \quad \rho_{e1} + (\rho_{t1} - \rho_{e1})/2 \leq \rho \leq \rho_{t1}$$
$$0, \quad \rho_{t1} < \rho \leq \rho_{e2}$$

$$\omega_3 = \frac{1}{2}, \quad \rho_{t2} \leq \rho < \rho_{e1}$$
$$\frac{1}{2}\cos^2\left(\pi\frac{\rho - \rho_{e1}}{\rho_{t1} - \rho_{e1}}\right), \quad \rho_{e1} \leq \rho < \rho_{e1} + (\rho_{t1} - \rho_{e1})/2$$
$$\cos^2\left(\pi\frac{\rho - \rho_{e1}}{\rho_{t1} - \rho_{e1}}\right), \quad \rho_{e1} + (\rho_{t1} - \rho_{e1})/2 \leq \rho \leq \rho_{t1}$$
$$1, \quad \rho_{t1} < \rho \leq \rho_{e2}$$

xi) $\rho_{e1} < \rho_{t2} \leq \rho_{e2} \leq \rho_{t1}$ $$\omega_1 = 1, \quad \rho_{e1} \leq \rho < \rho_{t2}$$
$$\cos^2\left(\pi\frac{\rho - \rho_{t2}}{\rho_{e2} - \rho_{t2}}\right), \quad \rho_{t2} \leq \rho < \rho_{t2} + (\rho_{e2} - \rho_{t2})/2$$
$$\frac{1}{2}\cos^2\left(\pi\frac{\rho - \rho_{t2}}{\rho_{e2} - \rho_{t2}}\right), \quad \rho_{t2} + (\rho_{e2} - \rho_{t2})/2 \leq \rho \leq \rho_{e2}$$
$$\frac{1}{2}, \quad \rho_{e2} < \rho \leq \rho_{t1}$$

$$\omega_2 = 0, \quad \rho_{e1} \leq \rho < \rho_{t2}$$
$$0, \quad \rho_{t2} \leq \rho < \rho_{t2} + (\rho_{e2} - \rho_{t2})/2$$
$$\frac{1}{2}\cos^2\left(\pi\frac{\rho - \rho_{t2}}{\rho_{e2} - \rho_{t2}}\right), \quad \rho_{t2} + (\rho_{e2} - \rho_{t2})/2 \leq \rho \leq \rho_{e2}$$
$$\frac{1}{2}, \quad \rho_{e2} < \rho \leq \rho_{t1}$$

$$\omega_3 = 0, \quad \rho_{e1} \leq \rho < \rho_{t2}$$
$$\sin^2\left(\pi\frac{\rho - \rho_{t2}}{\rho_{e2} - \rho_{t2}}\right), \quad \rho_{t2} \leq \rho < \rho_{t2} + (\rho_{e2} - \rho_{t2})/2$$
$$\sin^2\left(\pi\frac{\rho - \rho_{t2}}{\rho_{e2} - \rho_{t2}}\right), \quad \rho_{t2} + (\rho_{e2} - \rho_{t2})/2 \leq \rho \leq \rho_{e2}$$
$$0, \quad \rho_{e2} < \rho \leq \rho_{t1}$$

Although examples of weighting functions have been described above, it should be appreciated that the invention is not limited to these weighting functions. Other weighting functions may also be used, designed in substantially the same spirit of the design of the weighting functions described above.

Interpolation

Figure 22A:
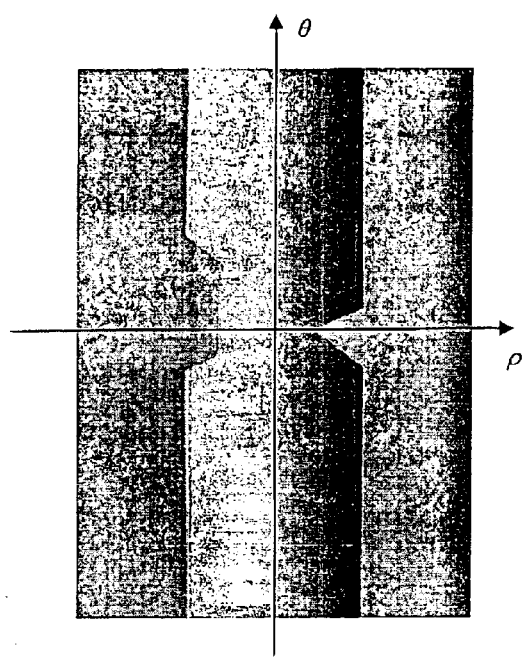
FIGS. 22(a) and (b) illustrate an exemplary first derivative radon data of the 3D Shepp-Logan phantom after data filling with zero padding and linear interpolation, respectively.
Figure 22B:
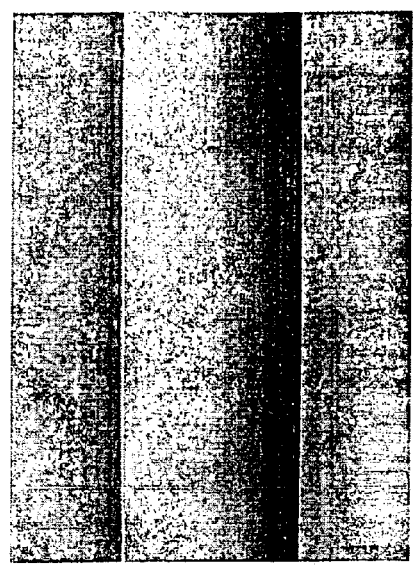
Figure 23A:
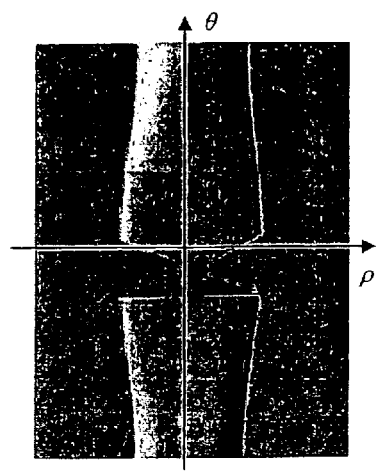
FIGS. 23(a)–(g) illustrate an exemplary first derivative Radon data of the 3D Shepp-Logan phantom at φ=90° for (a) group 1, (b) group 2, and (c) group 3, (d)(e)(f) weighting functions for each group and (g) combined data.
Figure 23B:
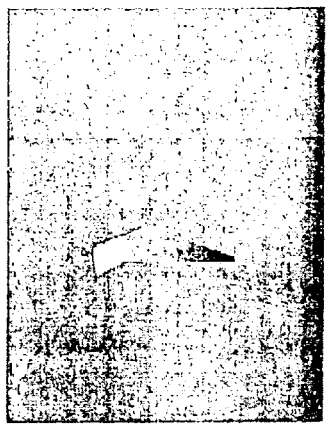
Figure 23C:
Figure 23D:
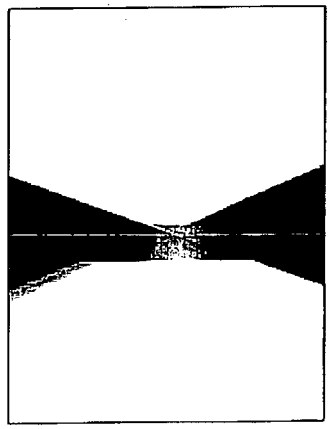
Figure 23E:
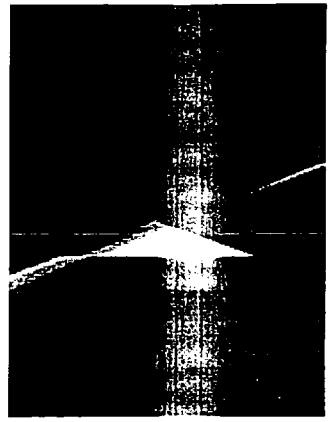
Figure 23F:
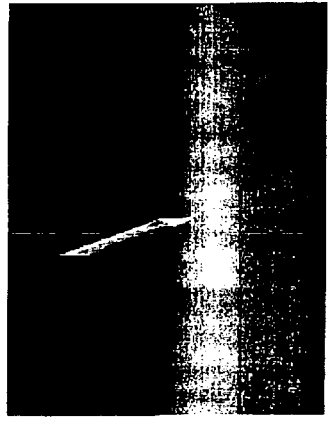
Figure 23G:

As in the circular scanning case described above, linear interpolation may also be used in the helical scanning case to estimate missing data. The boundaries of the shadow zone were numerically determined. Then, the shadow zones were linearly interpolated along the θ direction using the measured boundary values. To demonstrate this interpolation idea graphically, FIGS. 22(*a*)–(*b*) show the derivatives of Radon data with no interpolation and with linear interpolation, respectively.

It should be appreciated that other interpolation methods may also be used, designed in substantially the same spirit of the interpolation procedure described above.

Exemplary Implementation Procedure

To summarize, the Grangeat-type half-scan algorithm with a helical scanning locus can be implemented in the following exemplary steps:

(1) Specify a characteristic point $(\rho,\theta,\phi)$ where the derivative of Radon data can be calculated;
(2) Calculate $\lambda_{t1}$ and $\lambda_{t2}$;
(3) Calculate $\rho_{t1}$, $\rho_{t2}$, $\rho_{e1}$, $\rho_{e2}$;
(4) Calculate smooth weighting functions $\omega_1(\rho,\theta,\phi)$, $\omega_2(\rho,\theta,\phi)$, and $\omega_3(\rho,\theta,\phi)$;
(5) Determine line integration points for the given characteristic point according to appropriate rebinning equations;
(6) Calculate the derivatives of Radon data and store them according to their group membership as determined, according to one embodiment, by Eq. (23);
(7) Apply the weighting functions to the derivative of Radon data;
(8) Repeat Steps (1)–(7) until all the measurable characteristic points are done;
(9) Estimate the Radon data in the shadow zone (using the linear interpolation method according to one embodiment); and
(10) Use an inverse Radon formula to reconstruct an image volume.

According to an exemplary embodiment, results from steps (2)–(4) can be pre-calculated and stored for computational efficiency. Similarly, the rebinning coefficients from Step (5) can be found beforehand.

Exemplary Results

A software simulator was developed in the IDL Language (Research Systems Inc., Boulder, Colo.) for Grangeat-type image reconstruction. In the implementation of the Grangeat-type formula, the numerical differentiation was performed with a built-in function based on 3-point Lagrangian interpolation.

The source-to-origin distance was set to 5. The number of detectors per cone-beam projection was 256 by 256. The size of the 2D detector plane was 3.3 by 3.3. The helical pitch was 2. The full-cone angle was about 30 degree. The scan range was from 0 to $\pi+2\gamma_m$. The number of projections was 210. The number of meridian planes was 180. The numbers of radial and angular samples were 256 and 360, respectively. Each reconstructed image volume had dimensions of 4.1 by 4.1 by 4.1, and contained 256 by 256 by 256 voxels.

One might use the same number of projections above and below each and every slice so that all slices have the same image quality. In one approach, an asymmetric number of slices above and below the slice were used, except for the z=0 slice. If we use the symmetric half-scan helical Feldkamp, which has symmetric projections for any z location, all slices would have similar image quality. However, it means that each slice is reconstructed in a different time window.

According to this embodiment, a half-scan algorithm is provided in the Grangeat framework with superior temporal characteristics (temporal resolution and temporal consistency; the latter requires that a whole volume of interest is reconstructed with projections in the same time window) and less image artifacts (which is achieved by appropriate data handling in the shadow zone). The reason that the asymmetric projections were used was to maintain this temporal consistency. Half-scan helical Feldkamp methods may also be used in the same way.

The 3D Shepp-Logan phantom was used in the numerical simulation as shown in Table 2.

TABLE 2

Parameters of the phantoms used in our numerical simulation.

| Phantom | a | B | C | x | y | z | θ | φ | Density |
|---|---|---|---|---|---|---|---|---|---|
| Shepp-Logan | 0.69 | 0.9 | 0.92 | 0.0 | 0.0 | 0.0 | 0.0 | 0.0 | 2.0 |
| | 0.6624 | 0.88 | 0.874 | 0.0 | 0.0 | −0.0184 | 0.0 | 0.0 | −0.98 |
| | 0.41 | 0.21 | 0.16 | −0.22 | −0.25 | 0.0 | 0.0 | 72.0 | −0.02 |
| | 0.31 | 0.22 | 0.11 | 0.22 | −0.25 | 0.0 | 0.0 | −72.0 | −0.02 |
| | 0.21 | 0.35 | 0.25 | 0.0 | −0.25 | 0.35 | 0.0 | 0.0 | 0.01 |
| | 0.046 | 0.046 | 0.046 | 0.0 | −0.25 | 0.1 | 0.0 | 0.0 | 0.01 |
| | 0.046 | 0.02 | 0.023 | −0.08 | −0.25 | −0.605 | 0.0 | 0.0 | 0.01 |
| | 0.046 | 0.02 | 0.023 | 0.06 | −0.25 | −0.605 | 0.0 | 90.0 | 0.01 |
| | 0.056 | 0.1 | 0.04 | 0.06 | 0.625 | −0.105 | 0.0 | 0.0 | 0.02 |
| | 0.056 | 0.1 | 0.056 | 0.0 | 0.0625 | 0.1 | 0.0 | 0.0 | −0.02 |
| | 0.046 | 0.046 | 0.046 | 0.0 | −0.25 | −0.1 | 0.0 | 0.0 | 0.01 |
| | 0.023 | 0.023 | 0.023 | 0.0 | −0.25 | −0.605 | 0.0 | 0.0 | 0.01 |

In Table II, parameters of the phantoms used in our numerical simulation. (a,b,c) denote the semi-axes of ellipsoids, (x,y,z) the center coordinates of each ellipsoid, θ and φ the same as in FIG. 15. The actual density at a position is determined by summing the densities of the ellipsoids covering that point.

Figures 24A, 24B, 24C:
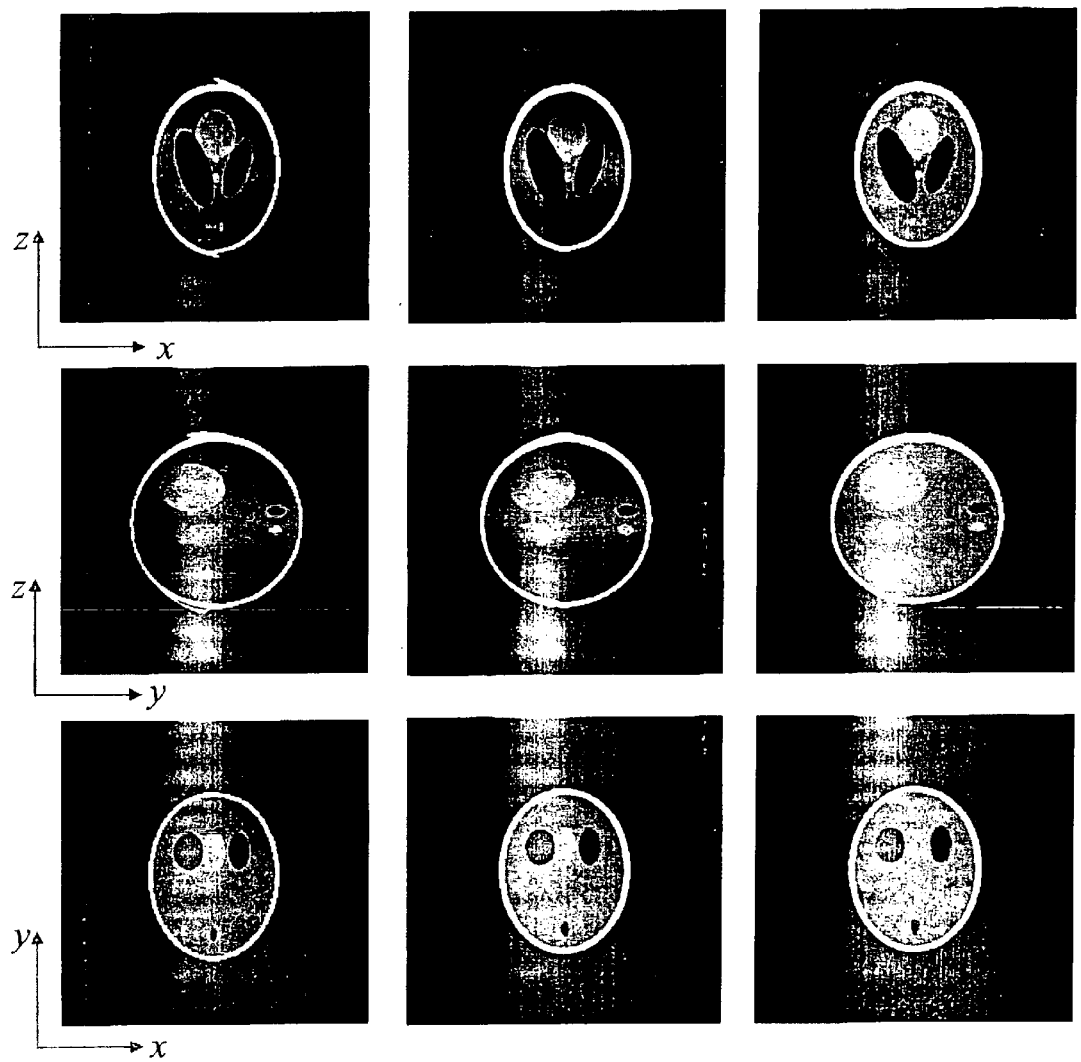
FIGS. 24(a) (b), and (c) illustrate exemplary reconstructed images of the 3D Shepp-Logan phantom for helical half-scan Feldkamp, Grangeat-type helical half-scan reconstruction with zero-padding and with linear interpolation, respectively.

FIG. 23 shows the derivatives of Radon data of the Shepp-Logan phantom, the weighting functions for each group, and the combined data. FIGS. 24(a)–(c) present typical reconstructed slices of the Shepp-Logan phantom. With the helical half-scan Feldkamp method (FIG. 24(a)) and the helical half-scan Grangeat and zero-padding method (FIG. 24(b)), the low intensity drop was serious away from the center plane. However, this type of artifacts was essentially eliminated with the helical half-scan Grangeat and linear interpolation method (FIG. 24(c)).

According to an exemplary embodiment, parallel-beam approximation of cone-beam projection data (in the spatial domain) may also be used to estimate missing data. In addition to the spatial domain approximation, the Radon domain estimation, such as linear interpolation, spline interpolation and knowledge-based interpolation, can be done in our framework as well. However, in the filtered backprojection framework, each frame of cone-beam projection data can be processed as soon as it is acquired, a desirable property for practical implementation.

According to exemplary embodiment, the strengths of the Radon space based algorithm described above may be combined with an algorithm for achieving high computational efficiency, e.g., that reported by Noo and Heuscher in the Defrise-Clack framework, described in Noo, F. and D. J. Heuscher, Image Reconstruction from cone-beam data on a circular short-scan, SPIE Medical Imaging, 2002, herein incorporated by reference. In this algorithm, a parallel-beam approximation is used to estimate missing cone-beam data due to the incompleteness of the half-scan.

The Radon space based algorithm yields more flexible data filling and can be modified for long object reconstruction, while the filtered backprojection algorithm provides high computational efficiency. Logically, we expect that in development of the Radon space based algorithm we will find the optimal strategy for missing data recovery; then we will seek for a filtered backprojection implementation of that algorithm without compromising the best achievable image quality. Our proposed filtered backprojection algorithm is similar to what has been described in the preceding subsection, except that we will apply a Noo-Heuscher-type filtered backprojection method for the short object reconstruction after using one of the following two filtered backprojection algorithms for the first order reconstruction:

The helical scanning geometry described herein solves the short object problem, which assumes that the object is completely covered by the X-ray cone beam from any source position. Even though research with the short object geometry is valuable on its own, such as for micro-CT imaging of spherical samples, the geometry for data truncation along the axial direction is the most practical. It should be appreciated that the Grangeat-type helical half-scan CT work may also be extended to the long object case, as described below.

According to yet another embodiment, the Grangeat-type half-scan algorithm described above may be used for reconstruction of a long object, which has important applications for clinical CT and biomedical micro-CT.

According to this embodiment, a temporally non-optimized pre-reconstruction step may be used to transform the long object problem into a short object problem. The detector area is analytically classified into desirable, corrupted, and useless areas. The cone-beam data in the corrupted area is corrected by the forward projection of the pre-reconstruction data, while data in the useless area is set to zero. Wang's generalized Feldkamp-type algorithm and Schaller's PHI algorithm may be used for the pre-reconstruction.

The Wang generalized Feldkamp algorithm is described, e.g., in Wang, G., et al., A General Cone-beam reconstruction algorithm, IEEE Trans. Med. Imaging, 1993, 12: pp. 483–496, herein incorporated by reference. This algorithm is approximate but efficient. Its half-scan version allows high temporal resolution but suffers from shading artifacts for a large cone angle.

The Schaller PHI algorithm is described, e.g., in Schaller, S., et al., Exact radon rebinning algorithms for the long object problem in helical cone-beam CT, IEEE Trans. Med. Imaging, 2000. 19(5), pp. 361–375. Tam proposed to scan along a helix and two circles, and avoid the truncated data in the rebinning framework. The Schaller PHI algorithm does not need the troublesome circles. In the Schaller method, Radon data on each meridian plane are calculated from the virtual object bounded by the helix lines instead of the two circles. Note that Radon data from the PHI algorithm are temporally poor due to the fact that the data are synthesized from several helical turns.

After the correction, the half-scan Grangeat method for the short object is applied along with several shadow zone interpolation techniques to correct the image artifacts. Specially designed temporal resolution phantoms are adopted to assess the image quality over the volume of interest. Comparison with a half-scan Feldkamp algorithm is conducted.

The Wang algorithm is the first effective yet simplest attempt to the long object problem, but the nature of the algorithm is only approximate and can be considered as the worst estimation. In our simulation, we achieved very similar image quality as we do in the short object case even with the worst estimation for the pre-reconstruction. The Schaller's method is very compatible with our general scheme and facilitates the Radon domain shadow zone interpolation. In conclusion, our proposed Grangeat-type half-scan strategy for solving the long object problem produces clearly superior image quality than Feldkamp-type algorithms, although its temporal resolution and image artifacts are substantially affected by the cone angle.

Exemplary Implementation Procedure

Figure 25A:
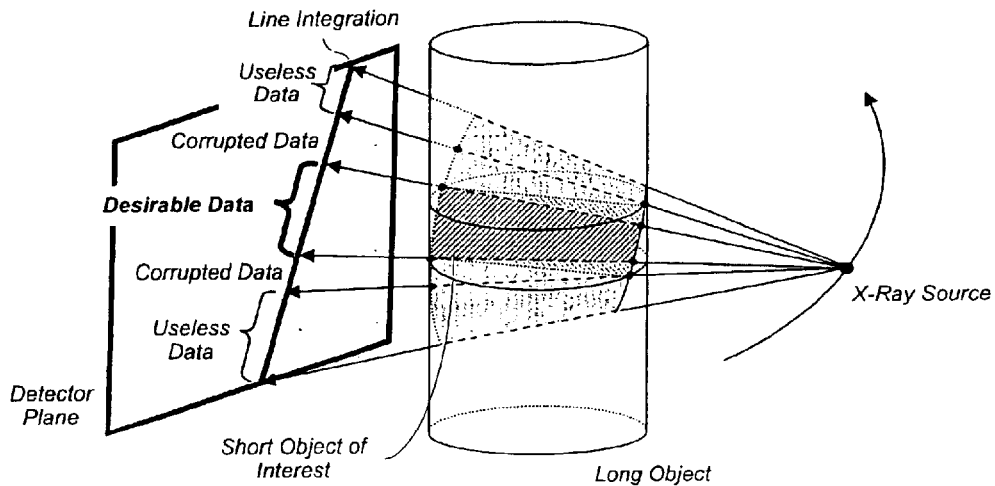
FIGS. 25(a) and (b) illustrate exemplary long object image reconstruction.
Figure 25B:
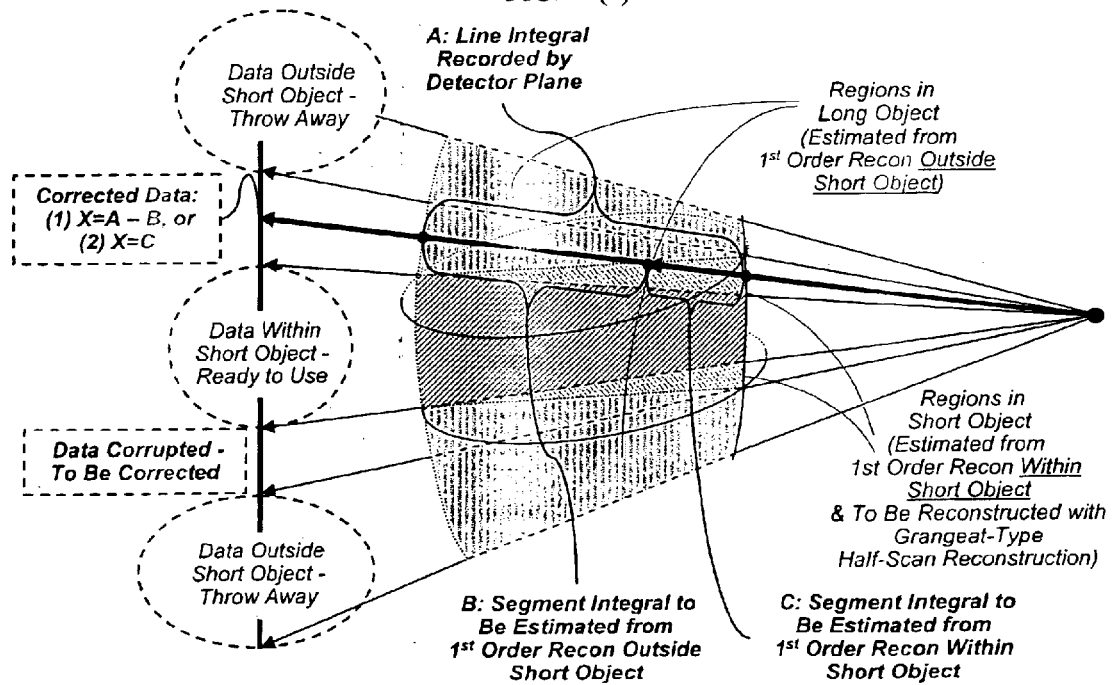

In general, the steps involved for long object image reconstructions are as follows (See FIG. 25).

(1) Select one of existing long object algorithms (none of which is optimized for the image quality we need, especially in terms of temporal resolution);

(2) Specify a volume of interest, which is the short object to be reconstructed;

(3) Perform the first-order reconstruction using the algorithm selected in (1). According to one embodiment, there are two possibilities: (3.1) reconstruct relevant regions outside the short object, and (3.2) reconstruct relevant regions inside the short object;

(4) Classify measured cone-beam data into (4.1) desirable, (4.2) corrupted, and (4.3) useless data (FIG. 7($a$)). The desirable data come exclusively from the short object, while the corrupted data involve structures inside and outside the short object, and the useless data carry no information on the short object;

(5) Correct the corrupted data based on forward projection of relevant voxel values in the first-order reconstruction. There are the two ways corresponding to the two possibilities in (3): (5.1) subtract segment integrals outside the short object from the measured cone-beam data, and (5.2) directly use segment integrals inside the short object;

(6) Estimate missing data on the shadow zone in the Radon space using forward projection of the first-order reconstruction and/or interpolation of Radon data derivatives calculated from measured cone-beam data;

(7) Perform necessary featuring between the data from the direct measures and the data from the first-order reconstruction;

(8) Perform our Grangeat-type half-scan reconstruction to reconstruct the short object for high temporal resolution.

The modification of our proposed algorithm into the filtered backprojection format will greatly improve its computational complexity.

Exemplary Simulation Results

Simulation of this embodiment revealed that image quality of the long object reconstruction is similar to that of the short object reconstruction. The Schaller's method is very compatible with this scheme, gives the benefits in the Radon domain data manipulation, and produces slightly better image quality than that with Wang's algorithm. The image artifacts are affected by the cone angle but are much less serious than that with the Feldkamp-type algorithm.

Throughout this application and attachments hereto, various publications may have been referenced. The disclosures of these publications in their entireties are hereby incorporated by reference into this application in order to more fully describe the state of the art to which this invention pertains. The publications disclosed are also individually and specifically incorporated by reference herein for the material contained in them that is discussed in the sentence in which the reference is relied upon.

The embodiments described above are given as illustrative examples only. It will be readily appreciated by those skilled in the art that many deviations may be made from the specific embodiments disclosed in this specification without departing from the scope of the invention. For example, although the embodiments described above have been directed to circular and helical scanning cases, it should be appreciated that the invention is also applicable to substantially circular and substantially helical, spiral, and spiral-like scanning cases.

What is claimed is:

1. A method for reconstructing an image of an object in a three-dimensional coordinate system with an x-ray computed tomography system, the method comprising the steps of:

conducting a partial scan of the object by rotating an x-ray beam having a cone beam geometry around a portion of the object or rotating the object in the x-ray beam, the x-ray beam forming a scanning trajectory through a plurality of projection lines from a plurality of successive focal point locations;

detecting the x-ray beam, attenuated by the object during the scan, to produce detector values;

integrating the detector values along the projection lines to obtain intermediate data; and calculating three-dimensional Radon values representing substantially accurate or approximate plane integrals of the object from the intermediate data using a Grangeat relationship.

2. The method of claim 1, wherein the step of conducting a partial scan includes rotating the x-ray beam around the object continuously or piece-wise continuously.

3. The method of claim 1, wherein the scanning trajectory is substantially circular.

4. The method of claim 1, wherein the scanning trajectory is substantially helical, spiral, or spiral-like.

5. The method of claim 1, wherein the step of integrating is performed explicitly.

6. The method of claim 1, wherein the step of integrating is performed implicitly.

7. The method of claim 1, wherein the step of calculating three-dimensional radon values uses a modified or extended version of the Grangeat relationship.

8. The method of claim 7, wherein in the modified or extended version of the Grangeat relationship comprising: a mosaic of truncated fan-beams used to cover a plane and estimate the radon value as the plane integral.

9. The method of claim 7, wherein in the modified or extended version of the Grangeat algorithm comprising: each characteristic point in the radon space categorized into singly, doubly, triply sampled, and shadow regions.

10. The method of claim 9, wherein each characteristic point is weighted appropriately to suppress image artifacts.

11. The method of claim 1, further comprising using at least one smooth weighting function to suppress data inconsistencies and associated image artifacts.

12. The method of claim 9, wherein the shadow regions are estimated by interpolation or extrapolation to remove artifacts due to missing information.

13. The method of claim 1, wherein the object is a short object.

14. The method of claim 1, wherein the object is a long object.

15. The method of claim 1, wherein the partial scan is less than 360 degrees.

16. A device for reconstructing an image of an object in a three-dimensional coordinate system with an x-ray computed tomography system, the device comprising:

a scanner for conducting a partial scan of the object by rotating an x-ray beam having a cone beam geometry around a portion of the object or rotating the object in the x-ray beam, the x-ray beam forming a scanning trajectory through a plurality of projection lines from a plurality of successive focal point locations;

detectors for detecting the x-ray beam, attenuated by the object during the scan, to produce detector values; and a processor for integrating the detector values along the projection lines to obtain intermediate data and calculating three-dimensional Radon values representing approximate or substantially accurate plane integrals of the object from the intermediate data using a Grangeat relationship.

17. The device of claim 16, wherein the scanner rotates the x-ray beam around the object continuously or piece-wise continuously.

18. The device of claim 16, wherein the scanning trajectory is substantially circular.

19. The device of claim 16, wherein the scanning trajectory is substantially helical, spiral, or spiral-like.

20. The device of claim 16, wherein the processor performs integration explicitly.

21. The device of claim 16, wherein the processor performs integration implicitly.

22. The device of claim 16, wherein the processor calculates three-dimensional Radon values using a modified or extended version of the Grangeat relationship.

23. The device of claim 22, wherein in the modified or extended version of the Grangeat relationship comprising: a mosaic of truncated fan-beams used to cover a plane and estimate the radon value as the plane integral.

24. The device of claim 22, wherein in the modified or extended version of the Grangeat algorithm comprising: each characteristic point in the radon space is categorized into singly, doubly, triply sampled, and shadow regions.

25. The device of claim 24, wherein each characteristic point is weighted appropriately to suppress image artifacts.

26. The device of claim 16, wherein the processor uses at least one smooth weighting function to suppress data inconsistencies and associated image artifacts.

27. The device of claim 24, wherein the shadow regions are estimated by interpolation or extrapolation to remove artifacts due to missing information.

28. The device of claim 16, wherein the object is a short object.

29. The device of claim 16, wherein the object is a long object.

30. The device of claim 16, wherein the scan is less than 360 degrees.

* * * * *